(12) United States Patent
Blaisdell et al.

(10) Patent No.: US 10,016,260 B2
(45) Date of Patent: Jul. 10, 2018

(54) ANATOMICAL HEALING ABUTMENTS, KITS, AND METHODS

(71) Applicants: Mark H. Blaisdell, Bountiful, UT (US); Todd C. Liston, Ogden, UT (US)

(72) Inventors: Mark H. Blaisdell, Bountiful, UT (US); Todd C. Liston, Ogden, UT (US)

(*) Notice: Subject to any disclaimer, the term of this patent is extended or adjusted under 35 U.S.C. 154(b) by 472 days.

(21) Appl. No.: 14/485,351

(22) Filed: Sep. 12, 2014

(65) Prior Publication Data

US 2015/0004563 A1 Jan. 1, 2015

Related U.S. Application Data

(63) Continuation-in-part of application No. 14/327,869, filed on Jul. 10, 2014, now Pat. No. 9,895,209, which is a continuation-in-part of application No. 14/152,369, filed on Jan. 10, 2014, now Pat. No. 9,572,640, which is a continuation-in-part of application No. 13/633,387, filed on Oct. 2, 2012, now Pat. No. 8,628,327, said application No. 14/327,869 is a continuation-in-part of application
(Continued)

(51) Int. Cl.
*A61C 11/00* (2006.01)
*A61C 8/00* (2006.01)
*A61C 13/34* (2006.01)

(52) U.S. Cl.
CPC ............ *A61C 8/008* (2013.01); *A61C 8/0001* (2013.01); *A61C 13/34* (2013.01)

(58) Field of Classification Search
CPC ................. A61C 8/00–8/0098; A61C 13/34
USPC .................................................. 433/172–176
See application file for complete search history.

(56) References Cited

U.S. PATENT DOCUMENTS

| 512,840 A | 1/1894 | Phelps |
| 1,335,372 A | 3/1920 | Fredericks |

(Continued)

FOREIGN PATENT DOCUMENTS

| WO | WO2010077130 | 7/2010 |
| WO | WO2010-141342 | 12/2010 |
| WO | WO2011-157762 | 12/2011 |

OTHER PUBLICATIONS

U.S. Appl. No. 13/633,387, filed Oct. 2, 2012, Blaisdell.
(Continued)

*Primary Examiner* — Yogesh Patel
(74) *Attorney, Agent, or Firm* — Workman Nydegger

(57) ABSTRACT

Anatomical healing abutments, kits and methods for promoting healing of gingival tissue around a subgingival void of a given tooth position. The abutment includes a cuff body having an anatomical subgingival portion extending from an implant end to the gingival margin of the patient, and an emergent crown portion extending occlusally from the subgingival portion beyond the gingival margin. A directional alignment body may be disposed on the cuff body and configured to extend bucally beyond an outer perimeter of the cuff body when the cuff body is anatomically aligned relative to the void. The subgingival portion has an asymmetric cross-section and is occlusally flared to anatomically fill the void and support gingival tissue around the void to minimize slump of tissue into the void. The crown portion has a mesial-distal width that spans a width of the gingival margin and an occlusal height to extend beyond the gingival margin.

9 Claims, 18 Drawing Sheets

Related U.S. Application Data

No. PCT/EP2013/020992, filed on Jan. 10, 2013, which is a continuation-in-part of application No. 13/633,387, filed on Oct. 2, 2012, now Pat. No. 8,628,327, and a continuation-in-part of application No. 13/347,127, filed on Jan. 10, 2012, now abandoned.

(56) References Cited

U.S. PATENT DOCUMENTS

| | | | |
|---|---|---|---|
| 2,475,599 | A | 7/1949 | Erdle |
| 3,286,350 | A | 11/1966 | Cooper |
| 4,001,938 | A | 1/1977 | Cooper |
| 4,986,753 | A | 1/1991 | Sellers |
| 5,071,345 | A | 12/1991 | Rosen |
| 5,180,303 | A | 1/1993 | Hornburg et al. |
| 5,324,186 | A | 6/1994 | Bakanowski |
| 5,338,196 | A | 8/1994 | Beaty et al. |
| 5,431,567 | A | 7/1995 | Daftary |
| 5,469,908 | A | 11/1995 | Chmel et al. |
| 5,492,471 | A | 2/1996 | Singer |
| 5,651,675 | A | 7/1997 | Singer |
| 5,658,147 | A | 8/1997 | Phimmasone |
| 5,674,069 | A | 10/1997 | Osorio |
| 5,695,337 | A | 12/1997 | Tyszblat Sodoun |
| 5,735,692 | A | 4/1998 | Berger |
| 5,738,518 | A | 4/1998 | Nowak |
| 5,813,858 | A | 9/1998 | Singer |
| 5,846,079 | A | 12/1998 | Knode |
| 5,871,358 | A | 2/1999 | Ingber et al. |
| RE36,126 | E | 3/1999 | Beaty et al. |
| 5,899,695 | A | 5/1999 | Lazzara |
| 5,911,580 | A | 6/1999 | Sharp et al. |
| RE36,689 | E | 5/2000 | Beaty et al. |
| 6,120,292 | A | 9/2000 | Buser |
| 6,155,828 | A | 12/2000 | Lazzara |
| 6,217,326 | B1 | 4/2001 | Hahn |
| 6,244,867 | B1 | 6/2001 | Aravena et al. |
| 6,283,753 | B1 | 9/2001 | Willoughby |
| 6,290,499 | B1 | 9/2001 | Lazzara et al. |
| 6,299,448 | B1 | 10/2001 | Zdrahala et al. |
| 6,300,390 | B1 | 10/2001 | Angeletakis |
| 6,361,721 | B1 | 3/2002 | Stern |
| 6,386,876 | B1 | 5/2002 | Lee |
| 6,431,867 | B1 | 8/2002 | Gittelson |
| 6,537,069 | B1 | 3/2003 | Simmons |
| RE38,630 | E | 10/2004 | Lazzara et al. |
| 7,018,207 | B2 | 3/2006 | Prestipino |
| 7,156,660 | B2 | 1/2007 | Huffman |
| 7,179,089 | B2 | 2/2007 | Sims et al. |
| 7,287,983 | B2 | 10/2007 | Ilan |
| 7,347,689 | B2 | 3/2008 | Huffan |
| 7,429,175 | B2* | 9/2008 | Gittelson ............... A61C 1/084 433/173 |
| 7,563,397 | B2 | 7/2009 | Schulman et al. |
| 7,632,095 | B2 | 12/2009 | Ostman et al. |
| D611,148 | S | 3/2010 | White, III |
| 7,762,814 | B2 | 7/2010 | van der Zel |
| 7,798,812 | B2 | 9/2010 | Last-Pollak |
| 7,816,423 | B2 | 10/2010 | Karim et al. |
| 7,922,488 | B2 | 4/2011 | Falk et al. |
| 7,922,490 | B2 | 4/2011 | Wen |
| 8,048,345 | B2 | 11/2011 | Feith |
| 8,105,081 | B2 | 1/2012 | Bavar |
| 8,382,477 | B2 | 2/2013 | Philibin |
| 8,628,327 | B1 | 1/2014 | Blaisdell et al. |
| 2001/0005575 | A1* | 6/2001 | Kanomi ............... A61C 7/00 433/18 |
| 2002/0064758 | A1 | 5/2002 | Lee |
| 2003/0170593 | A1 | 9/2003 | Dorfman |
| 2005/0040551 | A1 | 2/2005 | Biegler et al. |
| 2005/0048440 | A1 | 3/2005 | Feng |
| 2005/0084821 | A1 | 4/2005 | Sims et al. |
| 2006/0046229 | A1 | 3/2006 | Teich |
| 2006/0105296 | A1 | 5/2006 | Linder et al. |
| 2006/0263749 | A1 | 11/2006 | Koide |
| 2006/0286508 | A1 | 12/2006 | Bassett |
| 2007/0092853 | A1 | 4/2007 | Liu et al. |
| 2007/0111165 | A1* | 5/2007 | Wallick ............... A61C 8/0012 433/212.1 |
| 2008/0081317 | A1 | 4/2008 | White |
| 2008/0293013 | A1* | 11/2008 | Lussi ............... A61C 1/084 433/173 |
| 2008/0293016 | A1* | 11/2008 | Lussi ............... A61C 1/084 433/196 |
| 2008/0293017 | A1* | 11/2008 | Lussi ............... A61C 8/0012 433/196 |
| 2009/0081618 | A1 | 3/2009 | LaMar |
| 2009/0208906 | A1 | 8/2009 | Callan |
| 2010/0266985 | A1 | 10/2010 | Yau et al. |
| 2010/0279254 | A1 | 11/2010 | White |
| 2011/0008754 | A1 | 1/2011 | Bassett et al. |
| 2011/0081627 | A1 | 4/2011 | Sun et al. |
| 2011/0111368 | A1 | 5/2011 | Arnold et al. |
| 2011/0200968 | A1 | 8/2011 | Laizure, Jr. |
| 2011/0229859 | A1 | 9/2011 | White |
| 2011/0244426 | A1 | 10/2011 | Amber et al. |
| 2012/0022648 | A1 | 1/2012 | Vult Von Steyern |
| 2012/0052465 | A1 | 3/2012 | Von Both et al. |
| 2012/0164593 | A1 | 6/2012 | Bavar |
| 2013/0101964 | A1 | 4/2013 | Fudim |
| 2013/0177872 | A1 | 7/2013 | Blaisdell |
| 2017/0007372 | A1 | 1/2017 | Blaisdell |
| 2017/0128176 | A1 | 5/2017 | Vergoullis |
| 2017/0172714 | A1 | 6/2017 | Blaisdell |

OTHER PUBLICATIONS

U.S. Appl. No. 13/347,127, filed Jan. 10, 2012, Blaisdell.
U.S. Appl. No. 14/152,369, filed Jan. 10, 2014, Blaisdell et al.
U.S. Appl. No. 14/327,869, filed Jul. 10, 2014, Blaisdell et al.
U.S. Appl. No. 13/347,127, Mar. 25, 2013, Non-Final Office Action.
U.S. Appl. No. 13/633,387, Sep. 10, 2013, Notice of Allowance.
U.S. Appl. No. 13/347,127, Sep. 24, 2013, Final Office Action.
U.S. Appl. No. 13/347,127, Apr. 3, 2014, Non-Final Office Action.
PreFormance Post Cement-retained provisional option (Based on information and belief, available at least as early as Jan. 15, 2012).
Custom Temporary Components—https://www.inclusivedental.com/ToothReplacementSolutions/PartiallyEdentulous/InclusiveToothReplacementSolution/CustomTemporaryComponents.aspx. (Accessed Apr. 11, 2012).
"Contour Healer, The Superior Choice for Restorative Healing", http://contourhealer.com/about-us, Based on information and belief—Available at least as early as Dec. 13, 2012.
International Search Report and Written Opinion cited in PCT Application No. PCT/US2013/020992 dated Apr. 25, 2013.
Final Office Action for U.S. Appl. No. 13/347,127 dated Aug. 19, 2014, 20 pages.
Office Action for U.S. Appl. No. 14/152,369 dated Sep. 12, 2016, 5 pages.
Notice of Ailowance for U.S. Appl. No. 14/152,369 dated Oct. 13, 2016, 9 pages.
Office Action for U.S. Appl. No. 14/327,869 dated Mar. 6, 2017, 6 pages.
Notice of Allowance for U.S. Appl. No. 14/327,869 dated Oct. 30, 2017, 8 pages.

* cited by examiner

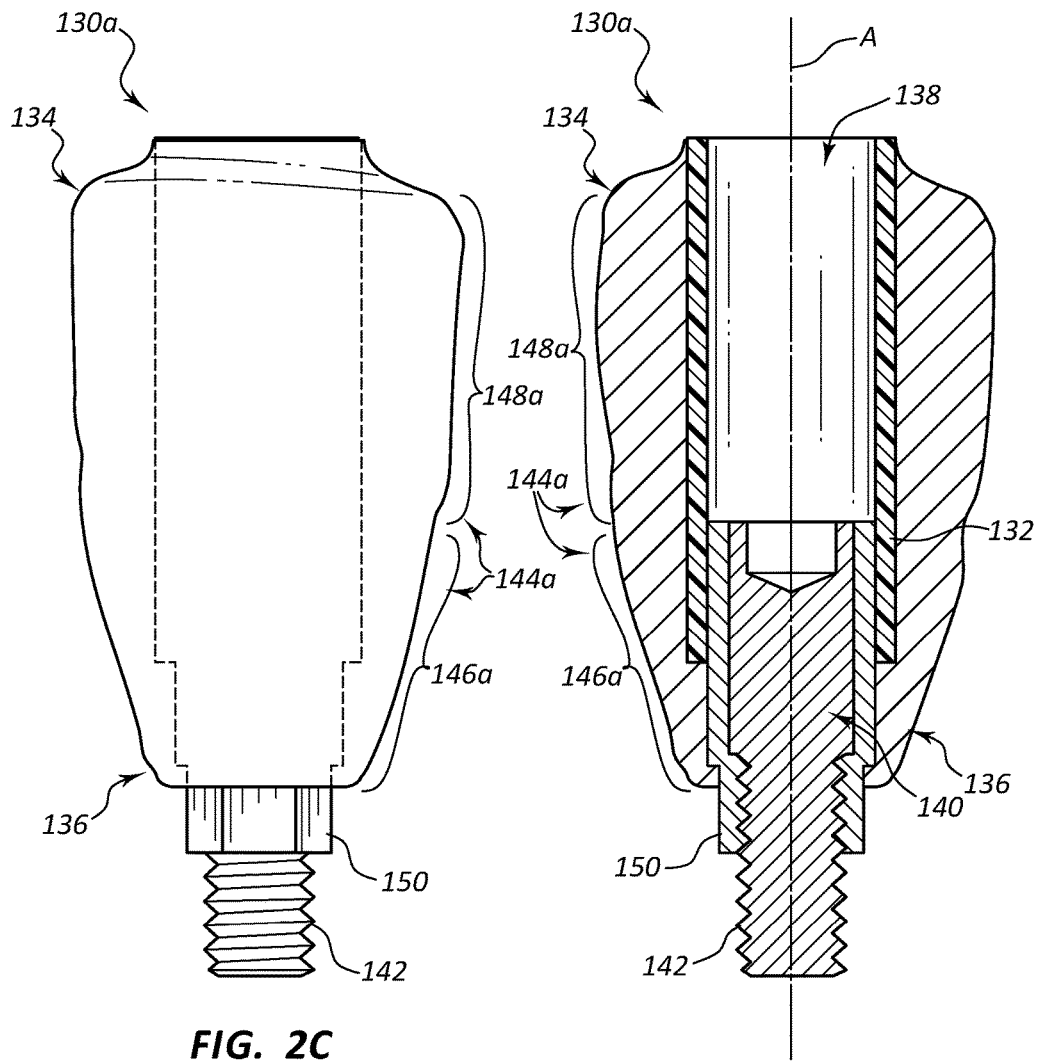
FIG. 2C
FIG. 2E
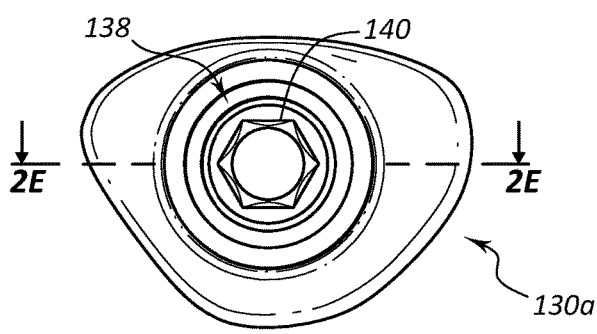
FIG. 2D

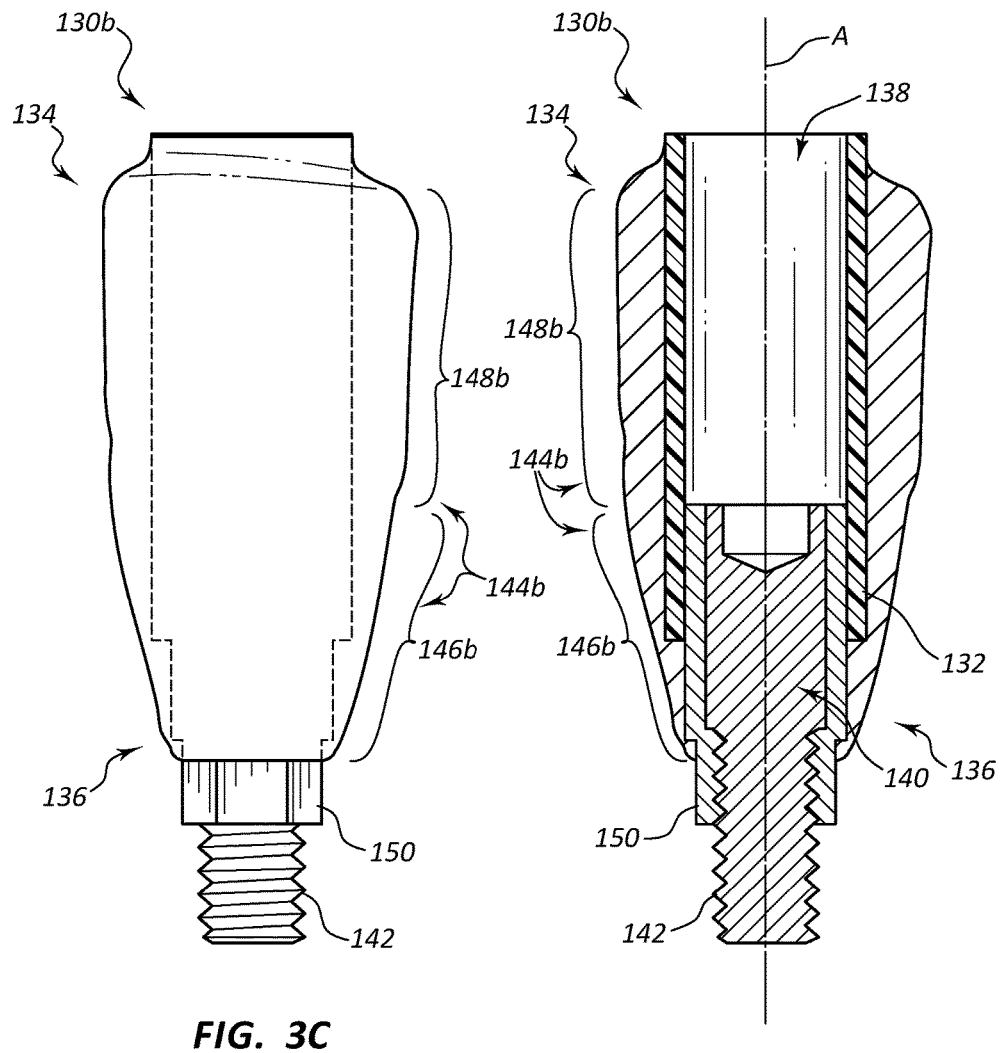
FIG. 3C
FIG. 3E
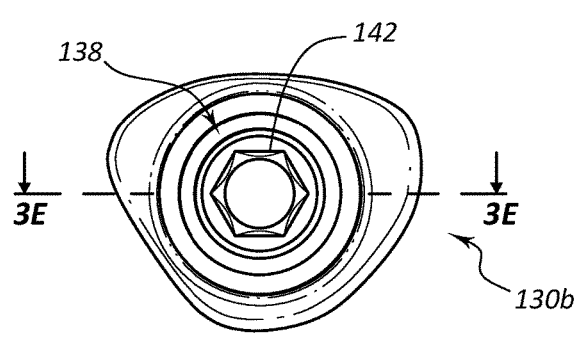
FIG. 3D

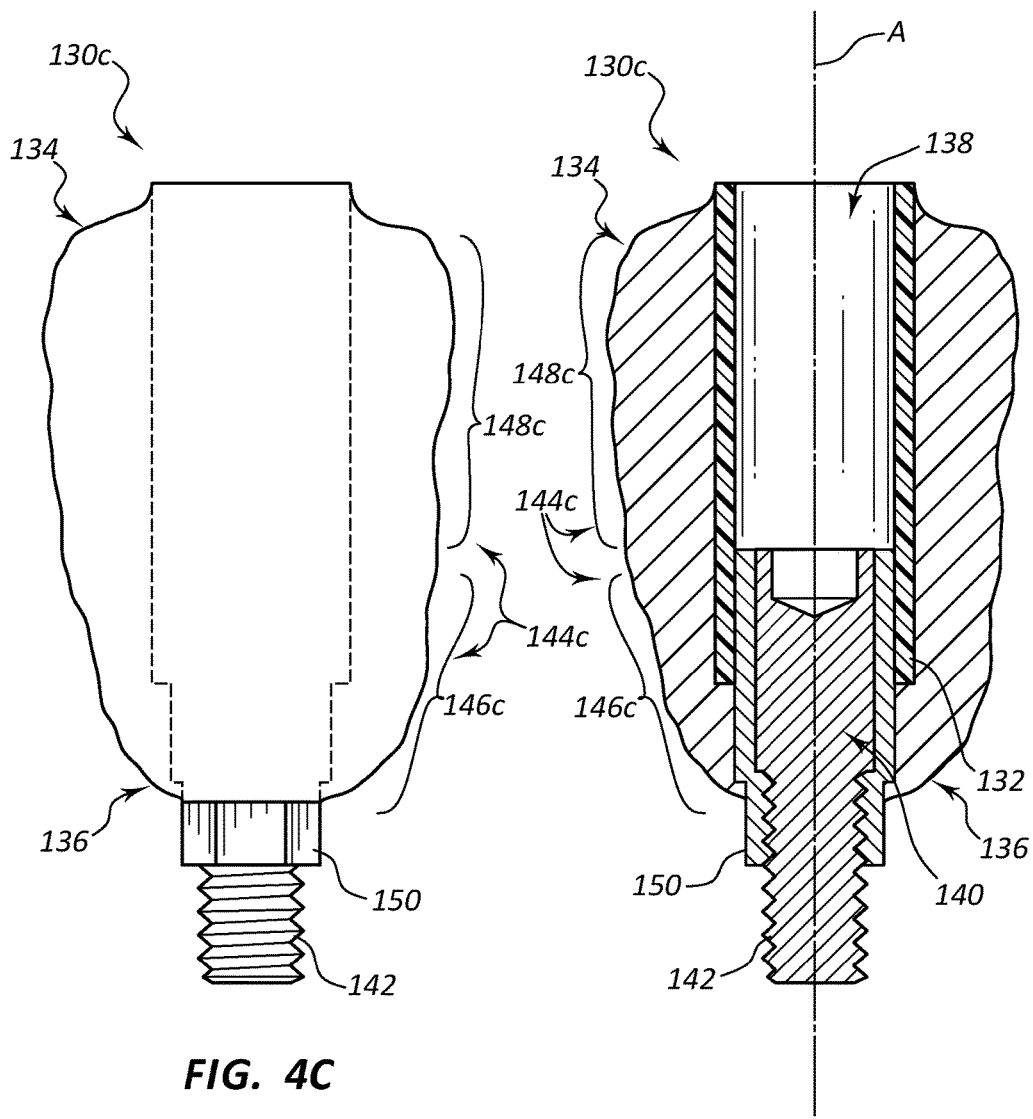
FIG. 4C
FIG. 4E
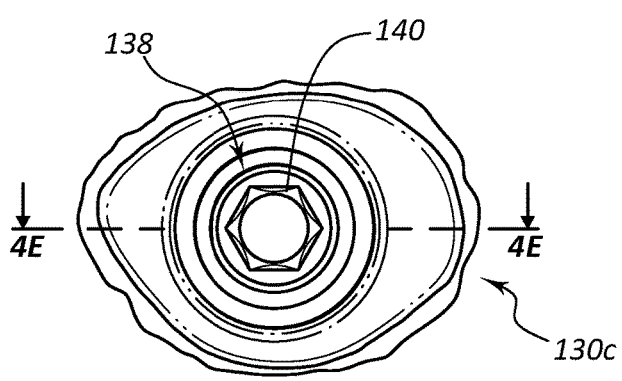
FIG. 4D

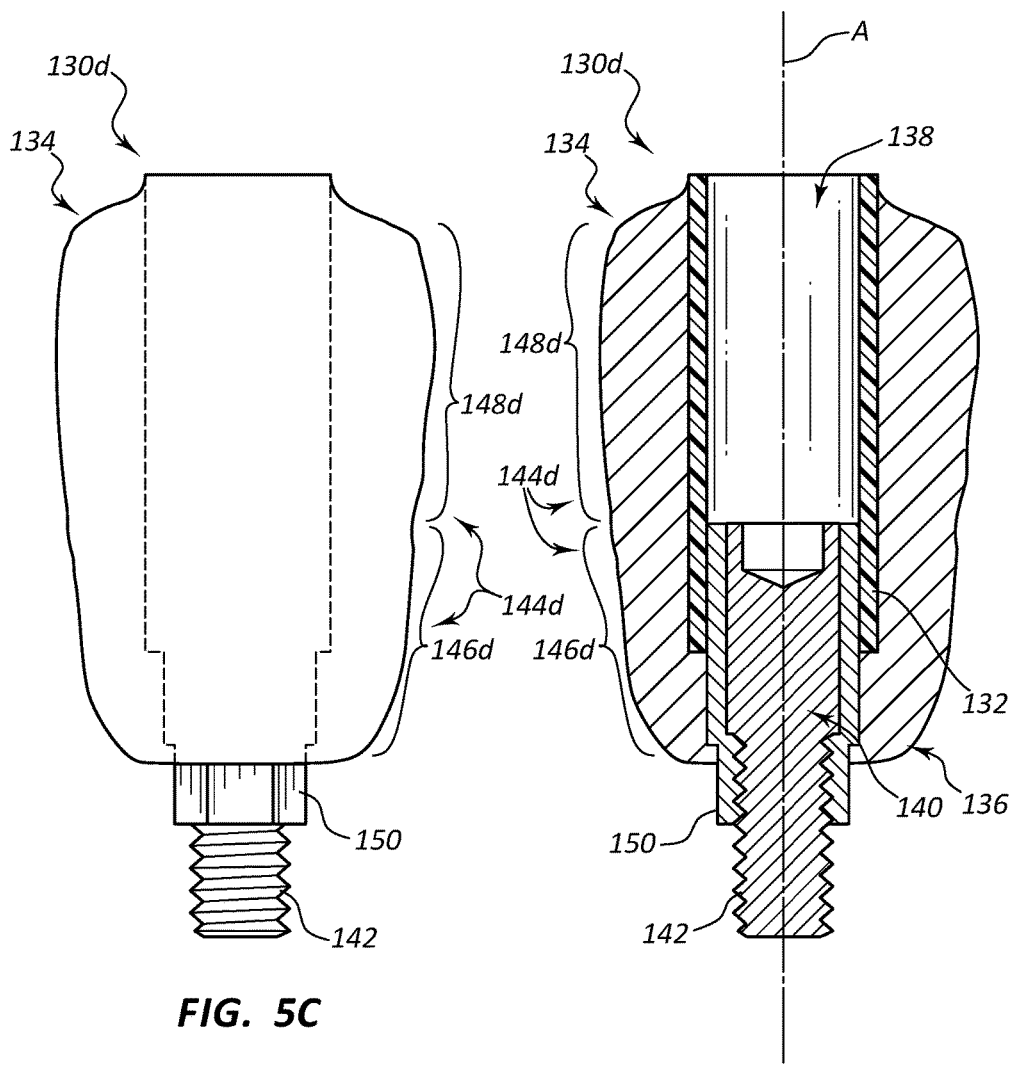
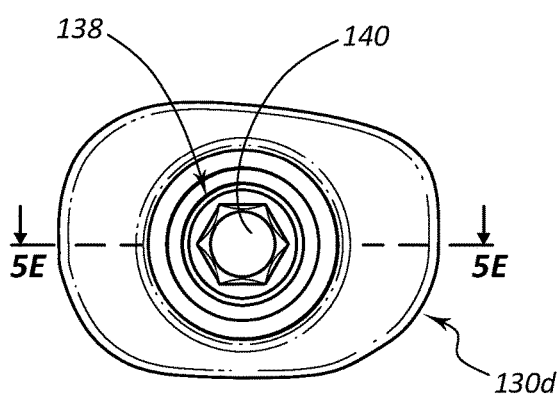
*FIG. 5C*
*FIG. 5D*
*FIG. 5E*

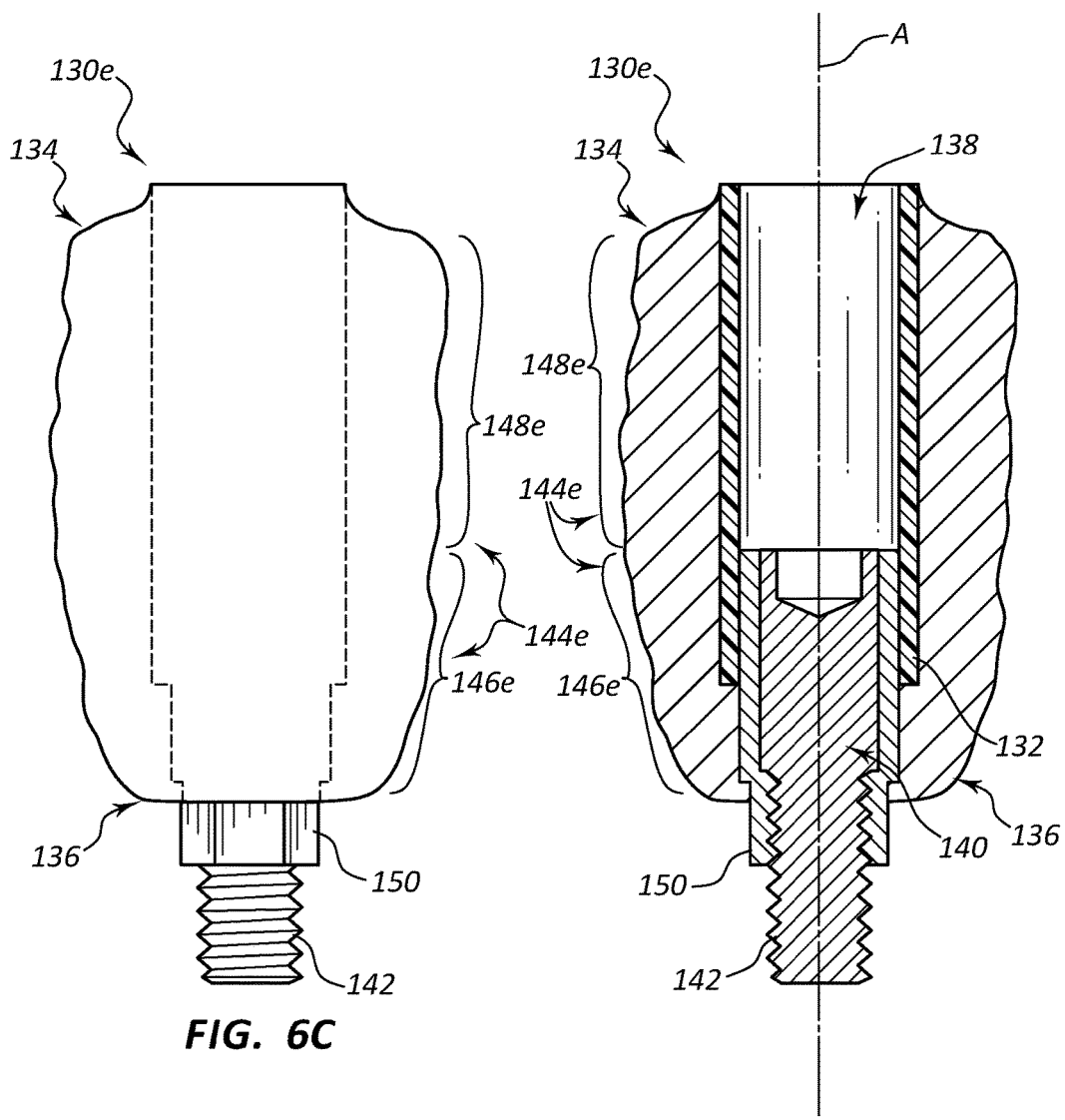
FIG. 6C
FIG. 6E
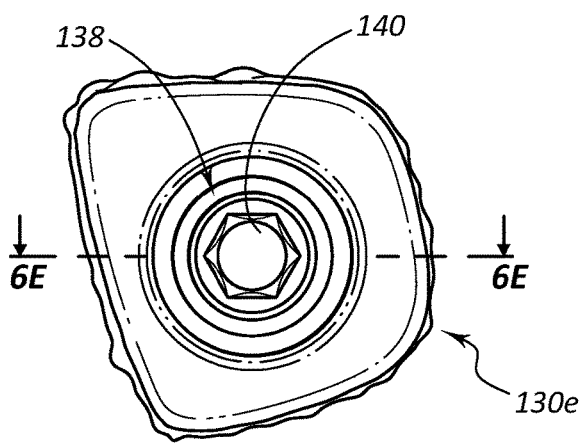
FIG. 6D

ANATOMICAL HEALING ABUTMENTS, KITS, AND METHODS

CROSS-REFERENCE TO RELATED APPLICATIONS

This Application is a continuation-in-part of U.S. patent application Ser. No. 14/327,869, filed Jul. 10, 2014, which is a continuation-in-part of U.S. patent application Ser. No. 14/152,369, filed Jan. 10, 2014, now U.S. Pat. No. 9,572,640, which is a continuation-in-part of U.S. patent application Ser. No. 13/633,387, filed Oct. 2, 2012, now U.S. Pat. No. 8,628,327. U.S. patent application Ser. No. 14/327,869, filed Jul. 10, 2014 is also a continuation-in-part of International Application No. PCT/US2013/020992, filed Jan. 10, 2013, which claims the benefit of U.S. patent application Ser. No. 13/633,387, filed Oct. 2, 2012, now U.S. Pat. No. 8,628,327, and U.S. patent application Ser. No. 13/347,127, filed Jan. 10, 2012. The disclosures of each of the foregoing applications are incorporated herein in their entirety.

BACKGROUND OF THE INVENTION

1. The Field of the Invention

Disclosed are healing caps or abutments used in oral surgery, more particularly anatomical healing caps or abutments, to promote healing of soft gingival tissue and preserve natural contour. Also disclosed are kits and methods that utilize anatomical healing caps or abutments.

2. Background and Relevant Art

In modern dentistry, when one or more teeth are removed it is desirable to eventually replace the tooth or teeth with a prosthesis (e.g., a crown, bridge, etc.), although this is typically accomplished months later. Once the tooth is removed or missing, a dental implant is placed into the bone tissue of the jaw to provide a secure foundation upon which a prosthesis can be supported. Typically, the site is allowed to heal for a period of time prior to installation of the permanent prosthesis. Currently, a device known as a healing cap, abutment, or cuff is coupled into the dental implant while the site is allowed to heal, to cap or cover the inside of the dental implant and to preserve the ability to re-access the dental implant once the site has sufficiently healed, when it is desired to install a prosthesis. Once the site has healed (e.g., typically 1.5 to 6 months after implant placement), the healing cap, abutment, or cuff is removed, and a custom prosthesis (e.g., a crown) may be installed, supported by the dental implant anchored within the jaw bone.

Existing dental healing caps, abutments, or cuffs, as well as the methods employed in their installation during immediate or subsequent dental placement and oral surgery exhibit several shortcomings.

BRIEF SUMMARY

The present invention is directed to abutments, kits, and methods for better preserving features of the gingival tissue that are characteristic surrounding a natural tooth. Such abutments, kits, and methods are helpful in preserving or creating desired gingival tissue characteristics whether a tooth is extracted or is congenitally or otherwise missing. According to one embodiment, an anatomical healing abutment for promoting healing of gingival tissue around a subgingival void of a given tooth position and shaping of a gingival margin of a patient at the given tooth position is provided. The anatomical healing abutment may include a cuff body having an anatomical subgingival portion extending from an implant end to the gingival margin of the patient, and an emergent crown portion extending from the subgingival portion and occlusally beyond the gingival margin of the patient. The anatomical healing abutment may include a directional alignment body disposed on the cuff body, and configured to extend bucally beyond an outer perimeter of the cuff body when the cuff body is anatomically aligned relative to the subgingival void of the given tooth position of the patient. The subgingival portion may have an asymmetric cross-section and is occlusally flared to anatomically fill and shape the subgingival void and support gingival tissue around the subgingival void to prevent or minimize slump of gingival tissue into the subgingival void. The emergent crown portion has a mesial-distal width so as to span a width of the gingival margin and an occlusal height so as to extend occlusally beyond the gingival margin.

Another embodiment is directed to an anatomical healing abutment for promoting healing of gingival tissue around a subgingival void of a given tooth position and shaping of a gingival margin of a patient at the given tooth position. The anatomical healing abutment may include a cuff body having an anatomical subgingival portion extending from an implant end to the gingival margin of the patient, and an emergent crown portion integrally formed with the subgingival portion, and extending beyond the gingival margin of the patient. By integrally formed, it is meant that both the subgingival portion and the emergent crown portion are formed from a single piece of material. The subgingival portion may have an asymmetric cross-section and may be occlusally flared to anatomically fill and shape the subgingival void and support gingival tissue around the subgingival void, prevent or minimize slump of gingival tissue into the subgingival void so as to substantially maintain or increase a height of contour of the gingival margin. The emergent crown portion may have an occlusal height so as to extend to at least the height of contour of the gingival margin, and a mesial-distal width so as to span a width of the gingival margin at the height of contour.

Because the subgingival voids of the various tooth positions are not identical to one another (but they do remain substantially the same from one person to another person when considering the same tooth position), different anatomical healing abutments are provided for the various tooth positions, which differ in the particular configuration of the subgingival portion of the cuff body of the respective healing abutment. For example, separately configured healing abutments may typically be provided for the upper central incisors, the upper lateral incisors, the upper cuspids, the upper bicuspids, and the upper molars. A set of healing abutments for the teeth of the lower dental arch may be similarly provided, e.g., lower incisors, lower cuspids, lower bicuspids, and lower molars. It may be possible to use identically configured healing abutments for some teeth (e.g., first and second bicuspids, first and second molars, or all lower incisors).

Accordingly, a kit of anatomical healing abutments for promoting healing of gingival tissue around a subgingival void of a given tooth position and shaping of a gingival margin of a patient at the given tooth position may include a plurality of differently sized and shaped healing abutments corresponding to subgingival voids of different tooth positions. The plurality of healing abutments may include a first healing abutment configured for treating a subgingival void of an incisor, a second healing abutment configured for treating a subgingival void of a cuspid or bicuspid, and a third healing abutment configured for treating a subgingival void of a molar position. Each healing abutment comprises a cuff body having an anatomical subgingival portion extending from an implant end to a gingival margin of the corresponding tooth position and an emergent crown portion extending from the subgingival portion and occlusally beyond the gingival margin. The anatomical subgingival portion of the cuff body may include an asymmetric cross-section and is occlusally flared so as to anatomically fill and shape the subgingival void of the corresponding tooth position and support gingival tissue around the subgingival void to prevent or minimize slump of gingival tissue into the subgingival void. The emergent crown portion may have a mesial-distal width so as to span a width of the gingival margin and an occlusal height so as to extend occlusally beyond the gingival margin of the corresponding tooth position.

A related method for promoting healing of gingival tissue around a subgingival void of a given tooth position and shaping of a gingival margin of a patient at the given tooth position may include providing an anatomical healing abutment. The healing abutment may include a cuff body having an anatomical subgingival portion having an asymmetric cross-section and an emergent crown portion extending occlusally from the subgingival portion. A directional alignment body may be provided on and extend beyond a perimeter of the cuff body. The subgingival portion of the anatomical healing abutment may be placed into the subgingival void, the alignment body may be manipulated to orient the healing abutment so that the anatomical subgingival portion is anatomically aligned relative to the subgingival void, the healing abutment may be fixed to a dental implant in communication with the subgingival void, and at least a portion of the directional alignment body may be removed from the fixed healing abutment.

These and other advantages and features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by references to specific embodiments thereof, which are illustrated in the appended drawings. It is appreciated that these drawings depict only typical embodiments of the invention and are therefore not to be considered limiting of its scope. The invention will be described and explained with additional specificity and detail through the use of the accompanying drawings in which:

FIG. 2C is a side elevation view of the anatomical healing abutment of FIG. 2B;

FIG. 2D is a top view of the anatomical healing abutment of FIG. 2B;

FIG. 2E is a cross-sectional view through the anatomical healing abutment of FIG. 2B;

FIG. 3C is a side elevation view of the anatomical healing abutment of FIG. 3B;

FIG. 3D is a top view of the anatomical healing abutment of FIG. 3B;

FIG. 3E is a cross-sectional view through the anatomical healing abutment of FIG. 3B;

FIG. 4C is a side elevation view of the anatomical healing abutment of FIG. 4B;

FIG. 4D is a top view of the anatomical healing abutment of FIG. 4B;

FIG. 4E is a cross-sectional view through the anatomical healing abutment of FIG. 4B;

FIG. 5C is a side elevation view of the anatomical healing abutment of FIG. 5B;

FIG. 5D is a top view of the anatomical healing abutment of FIG. 5B;

FIG. 5E is a cross-sectional view through the anatomical healing abutment of FIG. 5B;

FIG. 6C is a side elevation view of the anatomical healing abutment of FIG. 6B;

FIG. 6D is a top view of the anatomical healing abutment of FIG. 6B;

FIG. 6E is a cross-sectional view through the anatomical healing abutment of FIG. 6B;

DETAILED DESCRIPTION OF THE PREFERRED EMBODIMENTS

I. Introduction

Figure 1A:
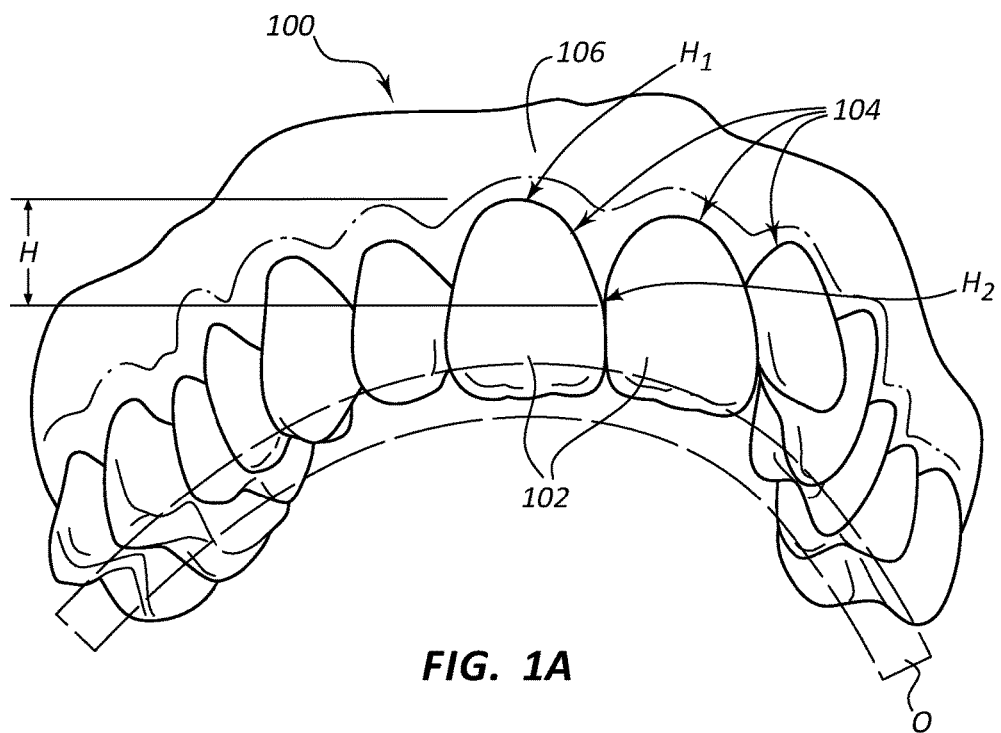
FIG. 1A is a perspective view of an exemplary upper dental arch.

One problem with conventional healing abutments and related methods of oral surgery is that those features of the gingiva that provide much of the characteristic natural aesthetic appearance of natural teeth and adjacent gum tissue are almost always lost once a tooth is pulled and replaced with a prosthesis. In particular, the gingival tissue surrounding the crown of a natural tooth where it emerges (i.e., its emergence profile) is lost during such procedures. For example, features such as the height of contour of the gingival margin is lost as the gingival tissue slumps into the void associated with the surgical site.

The gingival margin (also referred to as "cuff") refers to the generally scalloped pattern of the gingival tissue that is most prominently seen along the buccal surface of the teeth. The dynamic range of the height of contour of the gingival margin refers to the difference between the most occlusal extension of the gingiva (i.e., between teeth) as compared to its location at the gingival margin trough at the center of a tooth. Generally, the height of contour of the gingival cuff (i.e., its extension in an occlusal direction) is greatest at a location between two adjacent teeth. In other words, the location of the gingival margin extends occlusally to its greatest extent at this location between the teeth. At a location corresponding to a buccal center face of a tooth (at the gingival margin trough), the location of the gingival cuff exhibits its lowest occlusal extension ($H_1$ in FIG. 1A). The highest extension of the gingival margin ($H_2$ in FIG. 1A) may be referred to as the height of contour. For example, the present anatomical healing abutments may be configured so that the emergent crown portion of the abutment has an occlusal height that extends at least to the height of contour of the gingival margin. They may have a mesial-distal width so as to span a width of the gingival margin at the height of contour (i.e., the greatest occlusal direction extension of the gingival margin).

When a natural tooth is pulled and eventually replaced with a custom crown or other prosthesis, much of the dynamic range of the previous height of contour is lost because the gingival tissue between adjacent teeth recedes, and is lost.

Gingival tissue disposed between adjacent teeth is often referred to as the interdental papilla. This tissue resides between the void resulting from the pulled tooth and the adjacent remaining tooth. As a result of the loss of the tooth, the interdental papilla may atrophy and slump downward into the void over time. As a result, much of the interdental papilla tissue, particularly the initial and desirable aesthetic characteristics of this tissue, also tends to be lost upon removal of the natural tooth.

At the extreme gingival edge of the gingiva there is gingival tissue that overlies the underlying jaw bone. This gingival tissue (106 in FIG. 1A) typically exhibits a prominence in the buccal direction (i.e., it sticks out or protrudes bucally) and is often referred to as buccal prominence. While the gingival tissue over this bony tissue is not necessarily lost, the prominence by which the tissue sticks out bucally is typically lost when a natural tooth is pulled.

The present invention is directed to healing abutments, kits, and methods for better preserving these features of the gingival tissue surrounding a natural tooth that is pulled. The abutments, kits, and methods also aid in reconstructing or creating gingival tissue surrounding a tooth that was previously lost or congenitally missing. According to one embodiment, an anatomical healing abutment is provided. The anatomical healing abutment includes a cuff body having an anatomical subgingival portion that extends from an implant end to the gingival margin of the patient. An emergent crown portion of the cuff body extends from the subgingival portion, occlusally beyond the gingival margin of the patient. In other words, the gingival margin defines the transition between the subgingival and emergent crown portions. The anatomical subgingival portion includes an asymmetric cross-section and is occlusally flared so as to anatomically fill and shape the subgingival void to prevent or minimize slump of gingival tissue into the void, which void results upon removal of a selected tooth of a person's dental arch.

The anatomical healing abutment may further include a directional alignment body disposed on the cuff body, and configured to extend buccally beyond an outer perimeter of the cuff body when the cuff body is anatomically aligned relative to the void of the given tooth position of the patient. The emergent crown portion of the abutment has a mesial-distal width so as to span a width of the gingival margin, and an occlusal height so as to extend occlusally beyond the gingival margin, e.g., so that the emergent crown portion is visible in its extension in an occlusal direction from the subgingival portion (which resides below and up to the gingival margin). The "full" width of the emergent crown portion serves to ensure that adjacent teeth do not migrate mesially-distally towards the void, but remain in their desired positions, while also ensuring that all (100%) of the gingival tissue of the gingival margin is fully supported so as to prevent slump that otherwise occurs if the cuff body only provides support within a portion of the void, such as that of US2002/0064758 to Lee. Notwithstanding superficially similar teachings in Lee, Lee fails to show a device that fully supports the gingival tissue surrounding the subgingival void.

In addition, the cuff body may comprise a sculptable material (e.g., it is not formed of metal) so that a practitioner can remove select portions of the cuff body, add to the cuff body with a dental material that will adhere (e.g., curable composite, other curable dental materials, other adhering dental materials, etc.), or both. This allows the practitioner to chair-side fully customize the cuff body so that it provides a customized fit that custom fills the void resulting from removal of the selected tooth or aids in creating the desired natural gingival contours of a missing tooth.

Because the subgingival voids of the various tooth positions are not identical to one another (but they do remain substantially the same from one person to another person when considering the same tooth position), different anatomical healing abutments are provided for the various tooth positions, which differ in the particular configuration of the cuff body of the respective healing abutment. For example, separately configured healing abutments may typically be provided for the upper central incisors, the upper lateral incisors, the upper cuspids, the upper bicuspids, and the upper molars. A set of healing abutments for the teeth of the lower dental arch may be similarly provided, e.g., lower incisors, lower cuspids, lower bicuspids, and lower molars. It may be possible to use identically configured healing abutments for some teeth (e.g., first and second bicuspids, first and second molars, or all lower incisors).

FIGS. 1A-1F illustrate an upper dental arch, as well as typical steps employed in removal of a tooth, installation of an implant, and placement of a commercially available state of the art healing abutment. For example, FIG. 1A shows a person's upper dental arch 100 including central incisors 102. Also apparent in FIG. 1A is the scallop shaped gingival margin 104 where the natural teeth emerge from the gingival tissue, and the typical height of contour where the highest contour $H_2$ is between two adjacent teeth, while the lowest contour or point along the gingival cuff is $H_1$, at the trough of gingival margin 104, at the center of the buccal face of the teeth. The difference H between $H_2$ and $H_1$ represents the dynamic range of the height of contour associated with the natural teeth and gingival margin prior to removal of the natural tooth. It is this appearance that the present invention seeks to preserve, or to create in the instance of a congenitally missing or previously removed tooth.

Figure 1B:
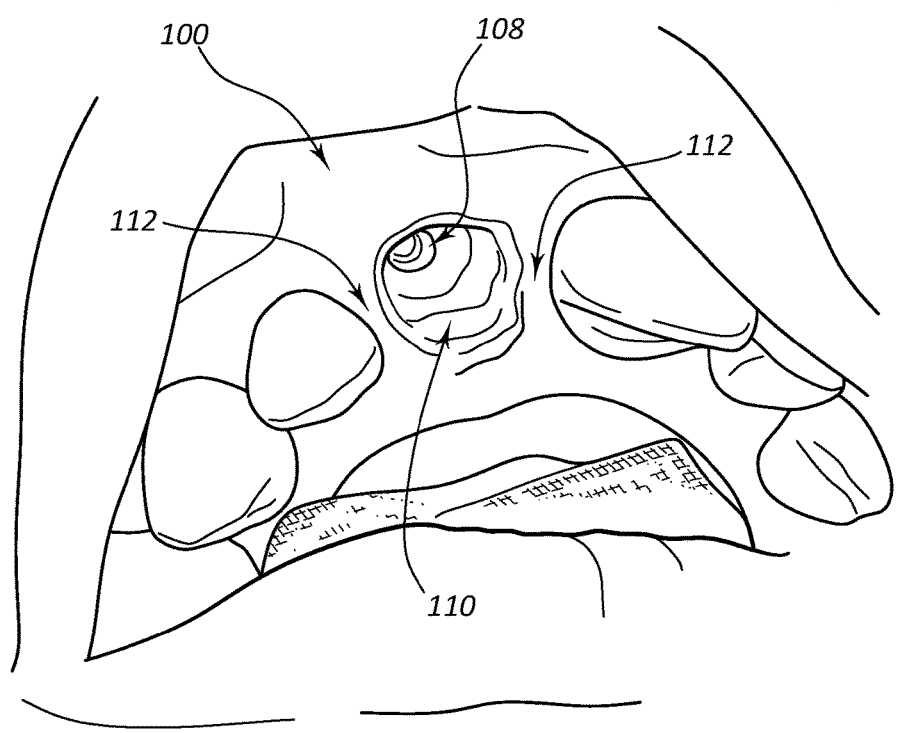
FIG. 1B is a perspective view of the dental arch of FIG. 1A in which a central incisor has been removed, leaving a void.

In addition to the gingival margin 104, a buccal prominence 106 is associated with the gingival edge of gingival margin 104, disposed gingivally relative to the crown of each respective tooth. FIG. 1B shows the dental arch 100 after central incisor 102 has been removed, leaving a void 108 once occupied by the root of tooth 102. The top or most gingival portion of void 108 may be termed the subgingival void 110, whose contours are defined by the shape of the subgingival portion of the tooth 102, just below the crown portion of the tooth. Also apparent in FIG. 1B is the interdental papilla 112.

The anatomical healing abutments of the present invention are specifically configured to preserve or restore or create (in the case of missing teeth) as much of this gingival tissue as possible.

Figure 1C:
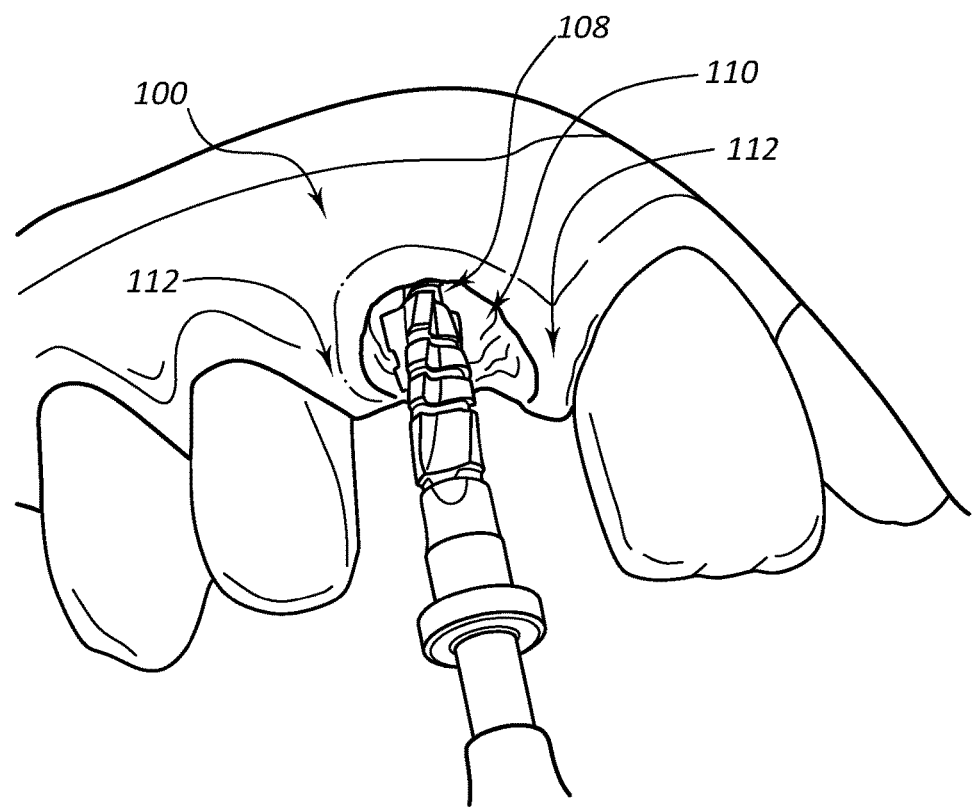
FIG. 1C is a perspective view of the dental arch of FIG. 1B in which a dental implant surgical drill is used to prepare an anchor hole in the underlying bone for anchoring a dental implant.
Figure 1D:
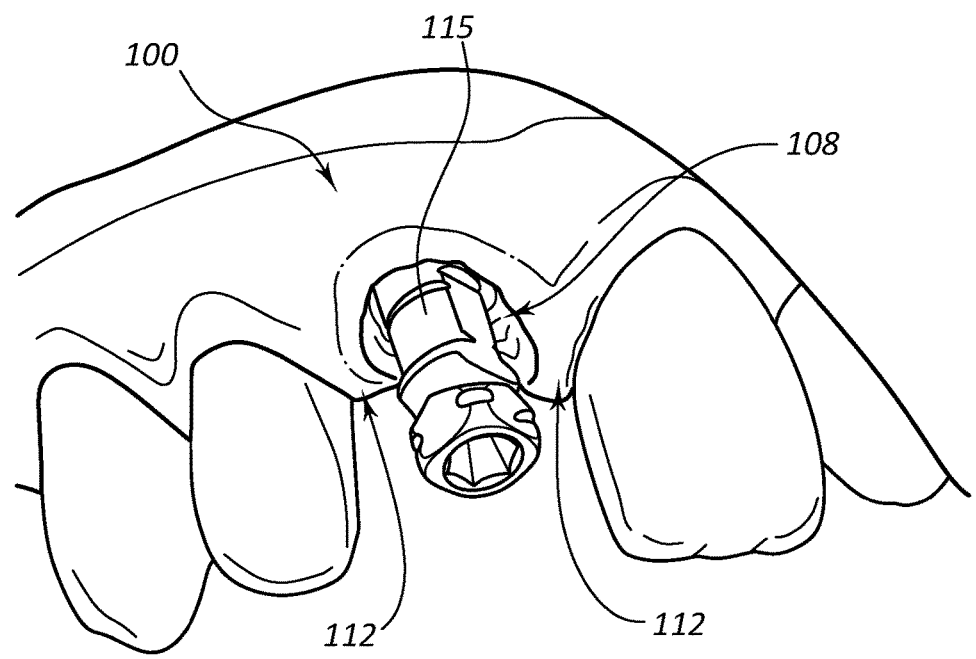
FIG. 1D is a perspective view of the arch of FIG. 1C as an implant is being inserted (e.g., with the aid of a transfer coping)
Figure 1E:
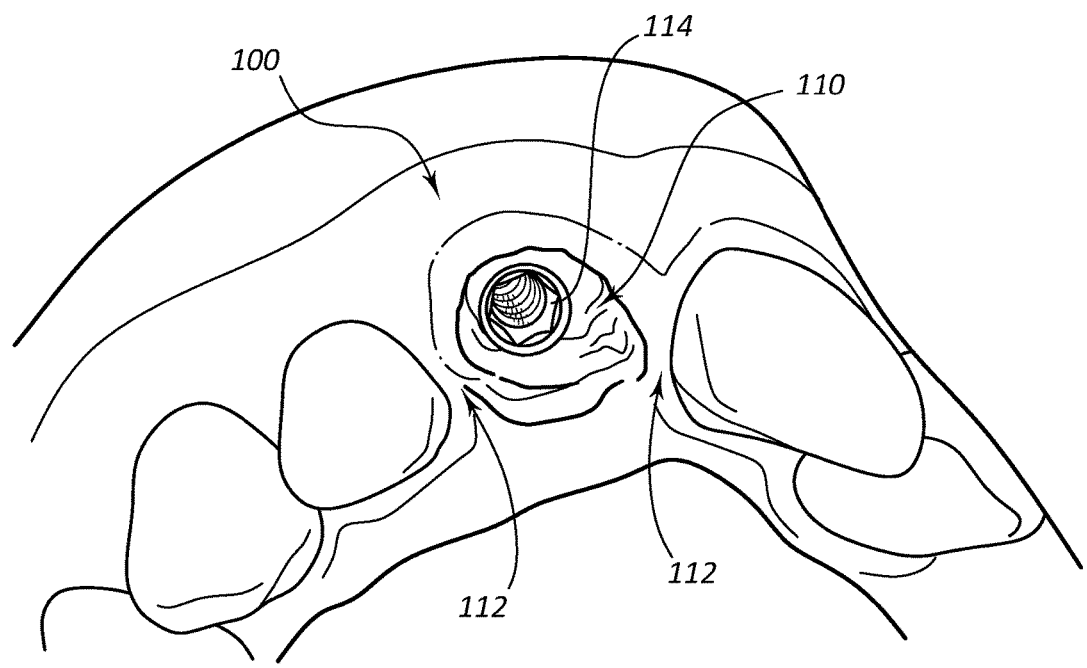
FIG. 1E is a perspective view of the arch and into the void showing the implant anchored into the bottom of the void.
Figure 1F:
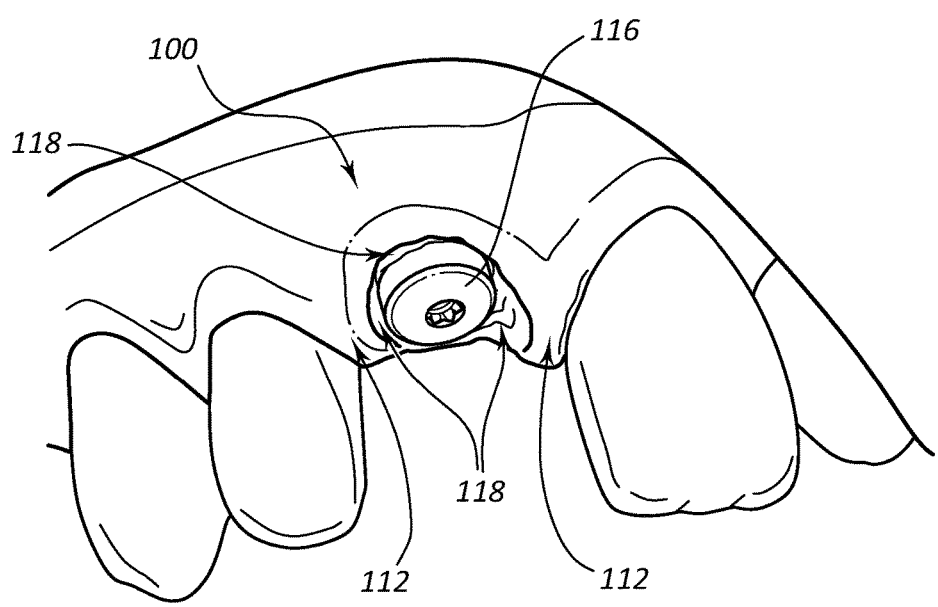
FIG. 1F is a perspective view of the arch showing a state of the art healing cuff coupled into the implant.

As shown in FIG. 1C, the void 108 is prepared to receive a dental implant 114 by drilling into the bone tissue of the underlying jaw bone at the bottom of void 108, after which a dental implant 114 may be inserted therein, as shown in FIG. 1D-1E. FIG. 1D shows a transfer coping 115 or similar structure being used to aid in seating the implant 114 into the bottom of void 108. FIG. 1E illustrates a view down into void 108 once dental implant 114 has been fully seated within the prepared underlying bony tissue (and transfer coping 115 has been uncoupled from implant 114). Some of the lower portion of void 108 may be filled by dental implant 114, while the subgingival void 110 remains unfilled. FIG. 1F shows installation of a state of the art healing abutment 116, which couples into dental implant 114. Healing abutment 116 is typically provided in various sizes, each of which is cylindrical (e.g., each of a different platform diameter ranging from about 3.5 mm to about 5.7 mm). A healing abutment is selected from the available sizes and coupled into dental implant 114. Healing abutment 116 may remain in place for several weeks (e.g., 1.5 to 6 months) while the site heals. As shown in FIG. 1F, because the healing abutment 116 is not anatomically shaped to fill the subgingival void 110, gaps 118 remain between healing abutment 116 and the gingival walls defining subgingival void 110. Placement of the healing abutment 116 may be the end of what is termed the first stage procedure. It will be understood that while described in terms of various stages, healing abutment 116 may be placed in various other oral surgery procedures (e.g., second stage, immediate placement, subsequent placement, etc.). Similarly, the inventive devices, kits and methods may be employed in various oral surgery procedures (e.g., during a first or second stage procedure, in an immediate placement procedure, in a delayed placement procedure, or in any other appropriate oral surgery procedure). The greatest benefit may be obtained where the inventive devices are placed immediately or soon after removal of a tooth and placement of the implant, so that the gingival tissue is immediately supported, and loss of desired gingival tissue features is minimized.

By way of example, in a subsequent second stage procedure, after a healing period of a few months, the person may return to the practitioner's office, the healing abutment 116 may be removed, and a permanent prosthesis may be installed by coupling into implant 114. During the healing period, the gingival tissue surrounding healing abutment 116 progressively adapts to the shape provided by healing abutment 116, collapsing into, growing into, or otherwise filling gaps 118. In addition, the dynamic range of the height of contour of the gingival cuff tends to be compressed (i.e., reduced) as the height of contour ($H_2$) recedes, tissue between adjacent teeth recedes, the interdental papilla fall, slump, or otherwise fill gaps 118, and the buccal prominence 106 recedes so as to be less prominent bucally. As a result, the original or desired gingival contours and other desirable gingival features are compromised. At this stage, even if one were to install a crown or other prosthesis that were a perfect match to the natural tooth, including the subgingival portion between the implant and the gingival margin, it is often too late to recapture the prior characteristics of the surrounding gingival tissue, which have been lost. Furthermore, when installing such a prosthesis at this later stage, the gingival tissue that has grown into gaps 118 is often cut away or compressed in order to make space for the prosthesis. Such activity can lead to subsequent necrosis of the gingival tissue.

III. Exemplary Anatomical Healing Abutments

FIGS. 2A-2E illustrate various views of an exemplary anatomical healing abutment 130a configured to fill the subgingival void resulting from removal of an upper central incisor. Anatomical healing abutment 130a may include an elongate body 132 extending between a proximal end 134 and a distal dental implant insertion end 136. Body 132 is advantageously hollow, including a hollow channel 138 with open ends and extending generally along longitudinal axis A so as to allow insertion of coupling screw member 140 into hollow channel 138, by which external threads 142 can be coupled into corresponding internal threads of a dental implant 114. In one embodiment, hollow channel 138 of body 132 may be bounded by a cylindrical or other shaped wall, which may or may not extend proximally above the top of cuff body 144a.

Healing abutment 130a advantageously includes an enlarged cuff body 144a extending laterally outward from hollow elongate body 132. In an embodiment, body 132 and body 144a are integral. In other words, they may be one and the same, such that no separate body 132 is present. This may be particularly so where cuff body 144a is formed of the same material (e.g., all as a single piece) as body 132. Of course, in other embodiments, bodies 132 and 144a may be distinct from one another (e.g., even formed of different materials). For example, cuff body 144a may be cast, molded, or otherwise formed about a core (e.g., body 132). Enlarged cuff body 144a is disposed between proximal end 134 and distal end 136, and includes a subgingival portion 146a that advantageously is shaped, as mass-manufactured, to anatomically fill subgingival void 110. Cuff body 144a further includes an emergent crown portion 148a, so that subgingival portion 146a becomes inserted within subgingival void 110 during use, while crown portion 148a resides gingivally above void 110 and the gingival margin. One or more directional alignment bodies 152, 154' may be provided on cuff body 144a, for use in manipulating and orienting subgingival portion 146a in the desired anatomical orientation relative to void 110, as will be described in further detail herein.

Portions 146a may be shaped to mimic the shape of the natural tooth which may have immediately prior resided within subgingival void 110. In particular, subgingival portion 146a is shaped to mimic that portion of the natural tooth which resides immediately below the gingival surface, so that this portion 146a mimics the portion of the natural tooth before and up to the point where it emerges from the gingival margin. In order to mimic the natural tooth contours just below the gingival surface, the subgingival portion 146a includes an asymmetric cross-section and is occlusally flared which mimics the profile of the natural tooth. This allows portion 146a to anatomically fill subgingival void 110 resulting from removal of an upper central incisor 102.

Emergent crown portion 148a may also be shaped to mimic the mesial-distal width and some shape characteristics of the natural tooth, particularly along the gingival margin, even though portion 148a resides above void 110. An emergence profile at the gingival margin is defined by the interface between the subgingival portion 146a and emergent crown portion 148a. It is advantageous to include an emergent crown portion so as to provide a surface that extends above the gingival tissue around the entire perimeter of the gingival margin, to better preserve the natural features of the gingival margin. For example, this provides support structure against which the gingival tissue can be supported and prevented from collapsing, even where the particular person's gingival margin profile may differ somewhat from the mass-manufactured subgingival portion 146a that approximates a custom fit. In one embodiment, the emergent crown portion 148a does not extend occlusally in height to the same extent that a normal natural tooth would. For example, occlusal features, including cusp features of the natural tooth may simply be omitted (e.g., the occlusal or top surface of the emergent crown portion 148a may simply be a generally flat surface, with a hole therein where hollow channel 138 intersects the generally flat surface.

While the occlusal height may differ somewhat from the natural, anatomical "normal" tooth, the mesial-distal width of the crown portion 148a may mimic that of the crown portion of the natural tooth at any given location of portion 148a. For example, the mesial-distal width may span the width of the gingival margin at each location along the gingival margin, including at the height of contour. Thus, the width of the crown portion 148a may not be reduced relative to the width of the anatomical, natural, normal tooth that resided or should reside at the given tooth position, but is present at its full width at each location of the gingival margin (i.e., so as to span the gingival margin at any given location). FIGS. 8C-8E illustrate this feature, showing portion 148a including a mesial-distal width W at the height of contour, between heights $H_2$ and $H_2$. It is also apparent from this Figure how the width of crown portion 148a has a mesial-distal width at all locations that are gingival to width W (as one moves from width W towards trough location $H_1$), which are also sufficient to span the width of the gingival margin. Spanning the gingival margin width along the entire gingival margin allows crown portion 148a to serve as a spacer, ensuring that adjacent teeth do not migrate from their desired positions inwardly, towards void 110, which may otherwise occur if cuff body 144a, including crown portion 148a is not present to prevent such movement. Furthermore, as described, the presence of crown portion 148a at the full mesial-distal width of the gingival margin 104 ensures that all gingival tissue of the entire gingival margin (e.g., including height of contour $H_2$, interdental papilla 112, etc.) are fully supported throughout the healing process.

The width of the emergent crown portion 148a may be at least equal to or greater in width at every location as compared to the greatest width of the subgingival portion, as shown in the Figures. A transition between the crown portion 148a and the subgingival portion 146a at the gingival margin may be smooth, rather than include any significant angled, sharp transitional steps in width along an exterior profile defined along the exterior width of the subgingival and crown portions. For example, along a transition (i.e., the gingival margin) between the subgingival and crown portions, there may be no more than a 25% reduction in width, no more than a 10% reduction in width, or no more than a 5% reduction in width. Preferably, there is no reduction in width, but if anything, an increase in width. The width along the entire length of the crown portion may be similarly characterized, e.g., no more than a 25% reduction in width, no more than a 10% reduction in width, or no more than a 5% reduction in width. Preferably, there is no reduction in width, but if anything, an increase in width. In other words, both any transition portion (e.g., the occlusal 10% of gingival portion 146a and the gingival 10% of crown portion 148a) and the crown portion itself may also include an occlusally flared profile, as does the subgingival portion 146a.

Reductions in width, particularly in a transition from the subgingival portion 146a to the crown portion 148a, interfere with the ability to bear against and support all of the gingival tissue, particularly the most occlusally disposed portions of the gingival tissue, such as height of contour H2 and the interdental papilla 112. They also interfere with the ability of the healing abutment to serve as a spacer, ensuring that adjacent teeth At least subgingival portion 146a of cuff body 144a may comprise a sculptable material so that a practitioner can easily remove select areas of portion 146a, can add to (i.e., build up) portion 146*a* with a dental material that will adhere (e.g., a curable dental material), or both so that portion 146*a* can be chair-side fully customized to provide an exact, custom anatomical fit that anatomically fills subgingival void 110. Sculptability is advantageous because while the shape and size of the subgingival void 110 is more or less the same for different persons for a particular given tooth position (e.g., generally all persons will have very similar subgingival voids for their upper central incisors), individual people do vary somewhat from individual to individual, and the ability to easily remove material, add material, or both relative to portion 146*a* allows the practitioner to fully customize portion 146*a* for a given subgingival void 110.

Of course, in some embodiments, more than a single size cuff body may be provided for any given tooth position. For example, children may exhibit differently sized subgingival voids as compared to adults for a given tooth position. Similarly, some individuals may have particularly large or small teeth, so that their subgingival voids may vary somewhat from the normal or average size. As such, in one embodiment, different sizes (e.g., normal adult size, a "large" adult size, a "small" adult size, and/or a child size) may be provided, such that the practitioner may choose the most appropriate size, which may then be fully customized by sculpting. Because the cuff body is sculptable, a practitioner may simply add to or remove material as needed to achieve the desired size.

In one embodiment, subgingival portion 146*a* may intentionally be sized to be slightly larger than the typical average subgingival void, so that the practitioner may shave or otherwise remove portions therefrom (e.g., with a dental burr, scalpel or other suitable tool) immediately prior to placement. This may be advantageous as it may be easier and less time consuming to typically require removal of material rather than supplementation, where material must be added to fully customize the subgingival portion 146*a*. In some embodiments, it may be expected that little or no modification (either removal or adding to) may be required. As such, the size and shape provided is already substantially configured to anatomically fill the person's subgingival void 110 (with substantially no gaps), providing the same emergence profile of cuff body at the gingival margin as was provided by the natural tooth to thereby support the gingival tissue.

In one embodiment, the subgingival portion 146*a*, and preferably the entire cuff body 144*a* is therefore not formed of metal, but comprises a material that may be easily and conveniently shaved or cut away, as well as added to. The subgingival portion 146*a* and emergent crown portion 148*a* may be integrally formed, from a single piece of sculptable material. Such suitable materials include any of various plastic materials, dental composite materials, or other materials that can be readily customizable through use of a dental burr, scalpel, or other suitable tool. In one embodiment a radiopaque filler may be incorporated into the plastic or composite so that the subgingival structures of the healing abutment can be viewed by x-ray or other imaging technique. Such materials also advantageously will readily bond to curable or other suitable adhering dental materials applied thereto where it is desired to add size or adjust contour to the as mass-manufactured cuff body. In one embodiment, the entire elongate body and enlarged cuff body may comprise a single piece of material (e.g., plastic or composite material).

Examples of radiopaque fillers include, but are not limited to a zirconia filled dental composite materials, or fillers including lanthanum, strontium, barium, zinc (e.g., zinc oxide).

In one embodiment, radiographic and/or position markers may be incorporated into the anatomical healing abutment. Such markers may be used to determine orientation, position, or other spatial information through a digital scanning or imaging process (e.g., CT scan, ultrasound, etc.) of the patient. Such markers may comprise any of the described radiopaque materials described above, or other suitable radiopaque materials (e.g., radiopaque metal alloys).

In one embodiment, commercially available temporary abutments may be used as a core about which the cuff body is formed. Such abutments are available from various manufacturers, e.g., Glidewell Laboratories, located in Newport Beach, Calif. Such temporary abutments employed as a core may be formed of any of various materials (e.g., including, but not limited to plastics, such as polyether ether ketone (PEEK), metal, ceramic (e.g., alumina, zirconia), etc.). Such temporary abutments may be formed by any suitable technique (e.g., casting, molding, machining, etc.) At least some such materials may similarly be suitable for use in forming the cuff body 144*a* and/or other portions of the presently described healing abutments. The inventors' earlier U.S. patent application Ser. Nos. 14/152,369; 14/327,869, and U.S. Pat. No. 8,628,327 describe casting jigs and methods for forming the anatomical healing abutments, each of which was incorporated by reference above.

In one embodiment, the exterior surface of cuff body 144*a*, particularly subgingival portion 146*a*, may be treated for stimulation of bone or other tissue growth. For example, the material of body 144*a* or portion 146*a* may be particularly selected so as to stimulate growth (e.g., a calcium containing material such as hydroxyapatite or similar bone growth promoting material), or the surface may be mechanically (e.g., roughened, smoothed, specific texture patterned), chemically, or otherwise treated to stimulate desired growth. While stimulation of bone growth may be desired, in another embodiment, material selection or treatment may be specifically configured to promote soft tissue growth.

In one embodiment, the distal dental implant insertion end 136 of anatomical healing abutment 130*a* may include a locking member 150 with a non-circular perimeter configured for insertion into a correspondingly shaped proximal end of a dental implant 114. In the illustrated configuration, the locking member 150 is hexagonal. Other configurations similarly configured to lock against rotation will be readily apparent to one of skill in the art (e.g., triangular, 4-sided, 5-sided, use of non-circular curved sides (e.g., an oval), combination of straight and curved sides, etc.). This locks the healing abutment 130*a* against rotation once inserted within the dental implant 114. Any suitable anti-rotation locking mechanism, including those proprietary to various dental implant manufacturers within the art, may be employed.

Figures 2A, 2B:
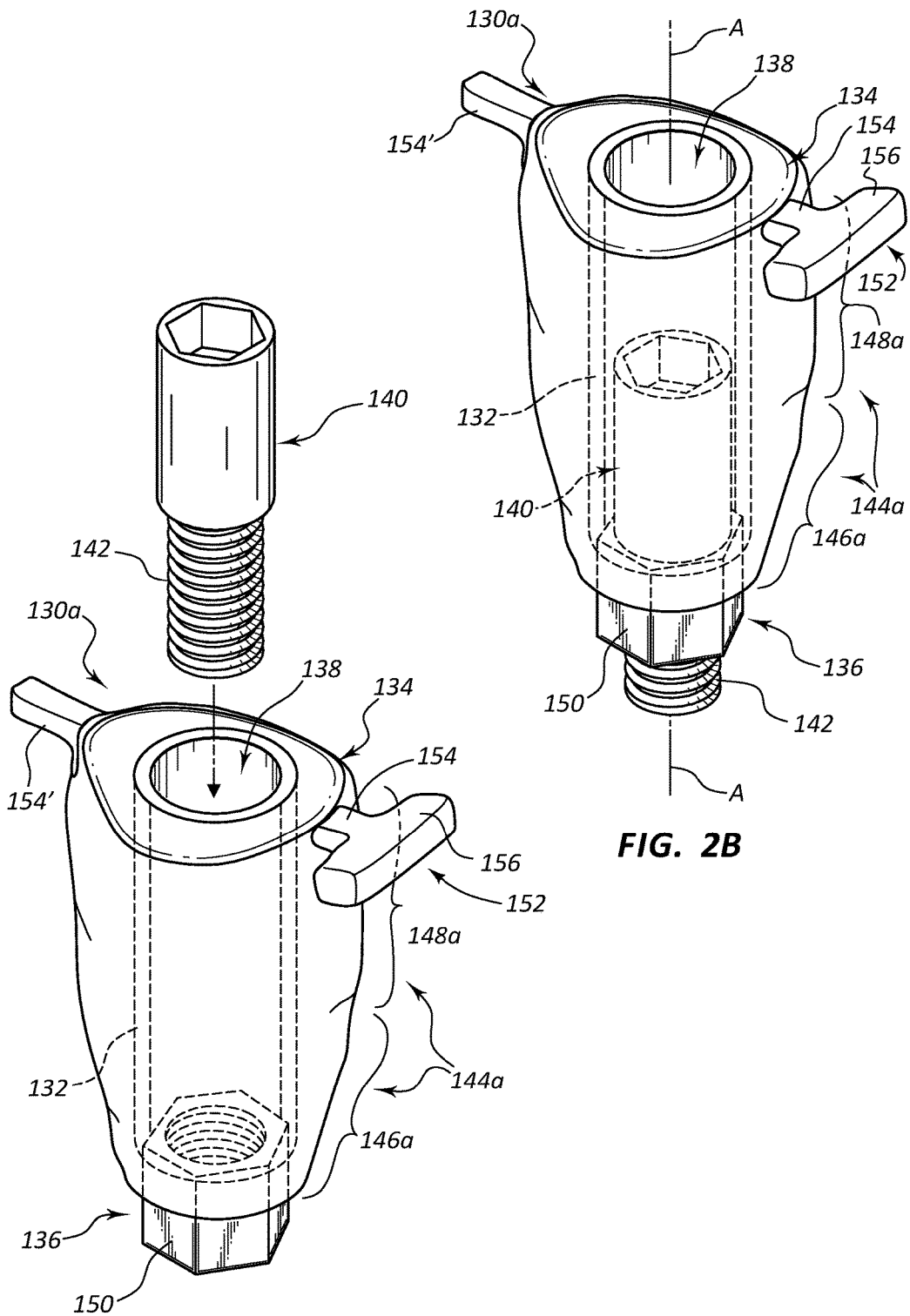
FIG. 2A is an exploded perspective view of an exemplary anatomical healing abutment according to the present invention including a cuff body having an anatomical subgingival portion and integral emergent crown portion, shown with a coupling screw.
FIG. 2B is an assembled perspective view of the anatomical healing abutment of FIG. 2A, with the coupling screw inserted in a central channel of the abutment.
Figure 2F:
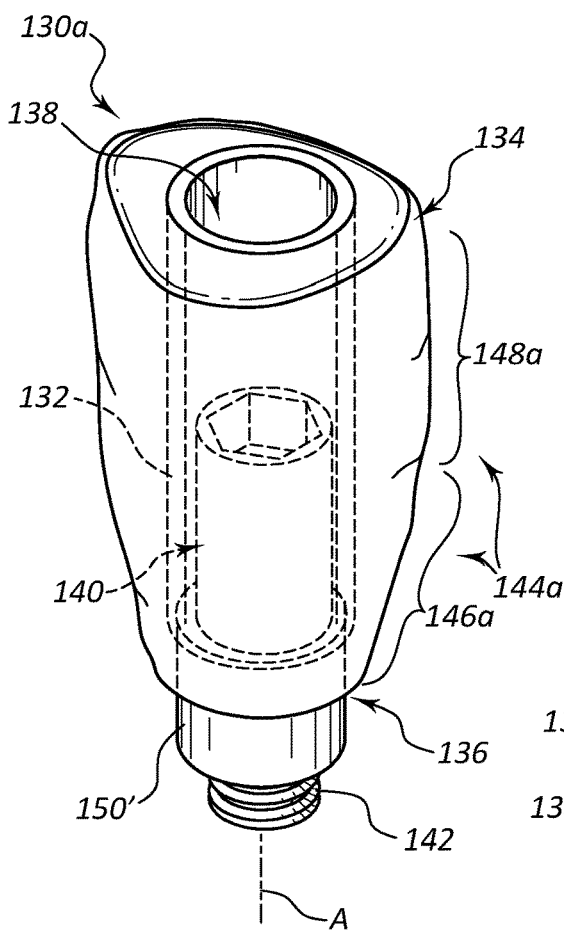
FIG. 2F is a perspective view similar to that of FIG. 2B, but showing an alternative locking structure at the distal dental implant end.
Figure 2G:
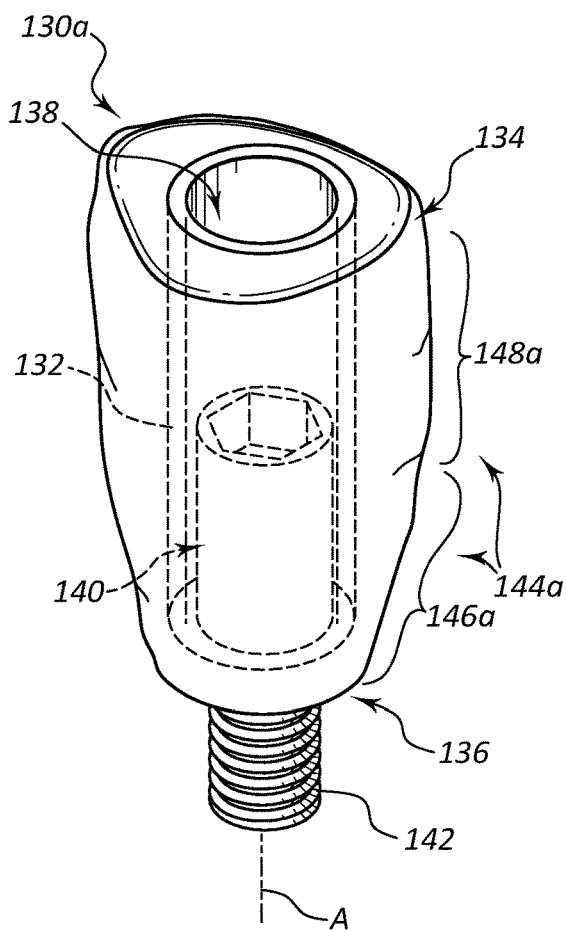
FIG. 2G is a perspective view similar to that of FIG. 2B, but showing another a distal dental implant end with no locking structure.
Figures 3A, 3B:
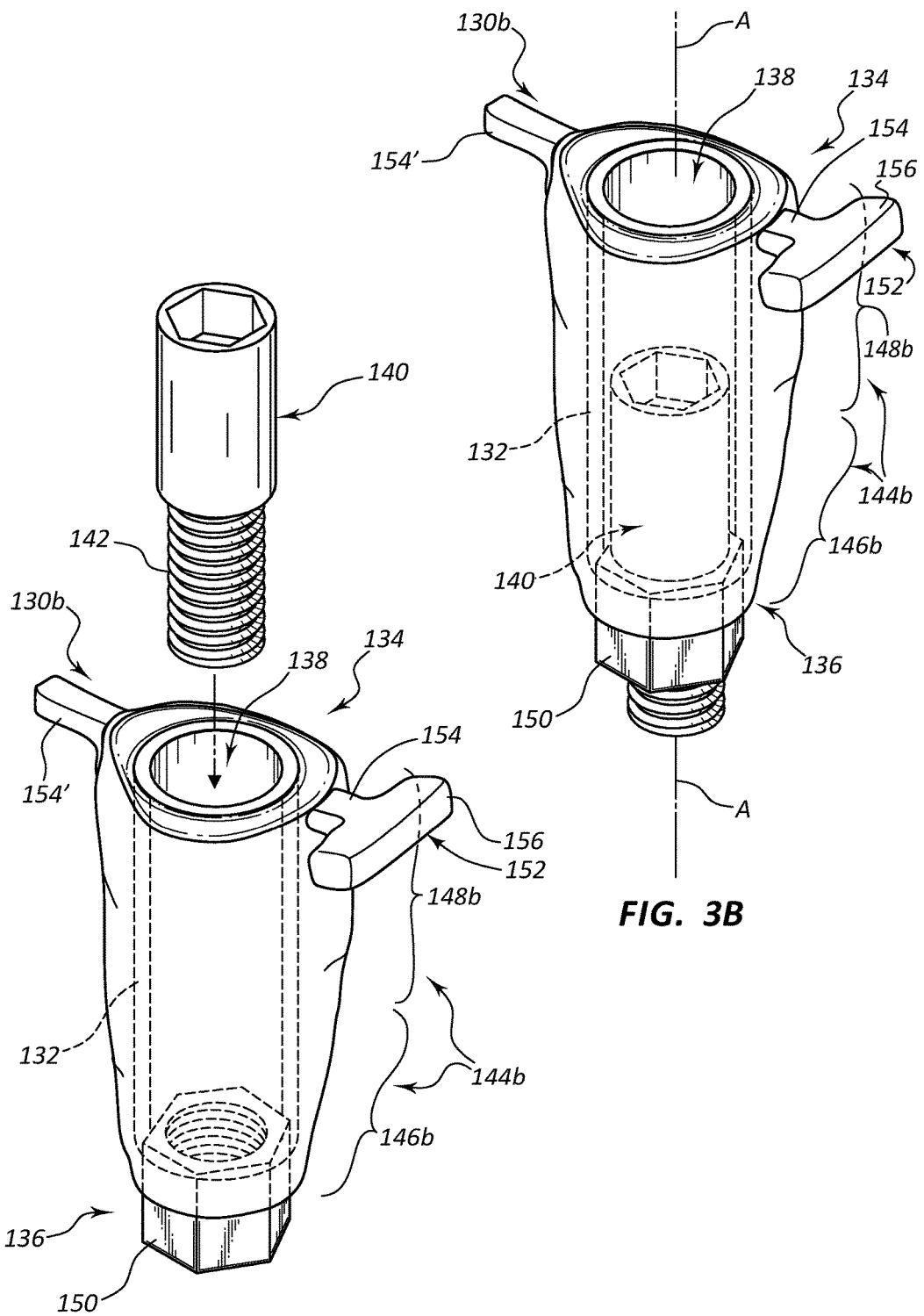
FIG. 3A is an exploded perspective view of a coupling screw and an anatomical healing abutment specifically configured for the upper lateral incisor tooth position.
FIG. 3B is an perspective view of the anatomical healing abutment of FIG. 3A with the coupling screw in the central channel of the abutment.
Figures 4A, 4B:
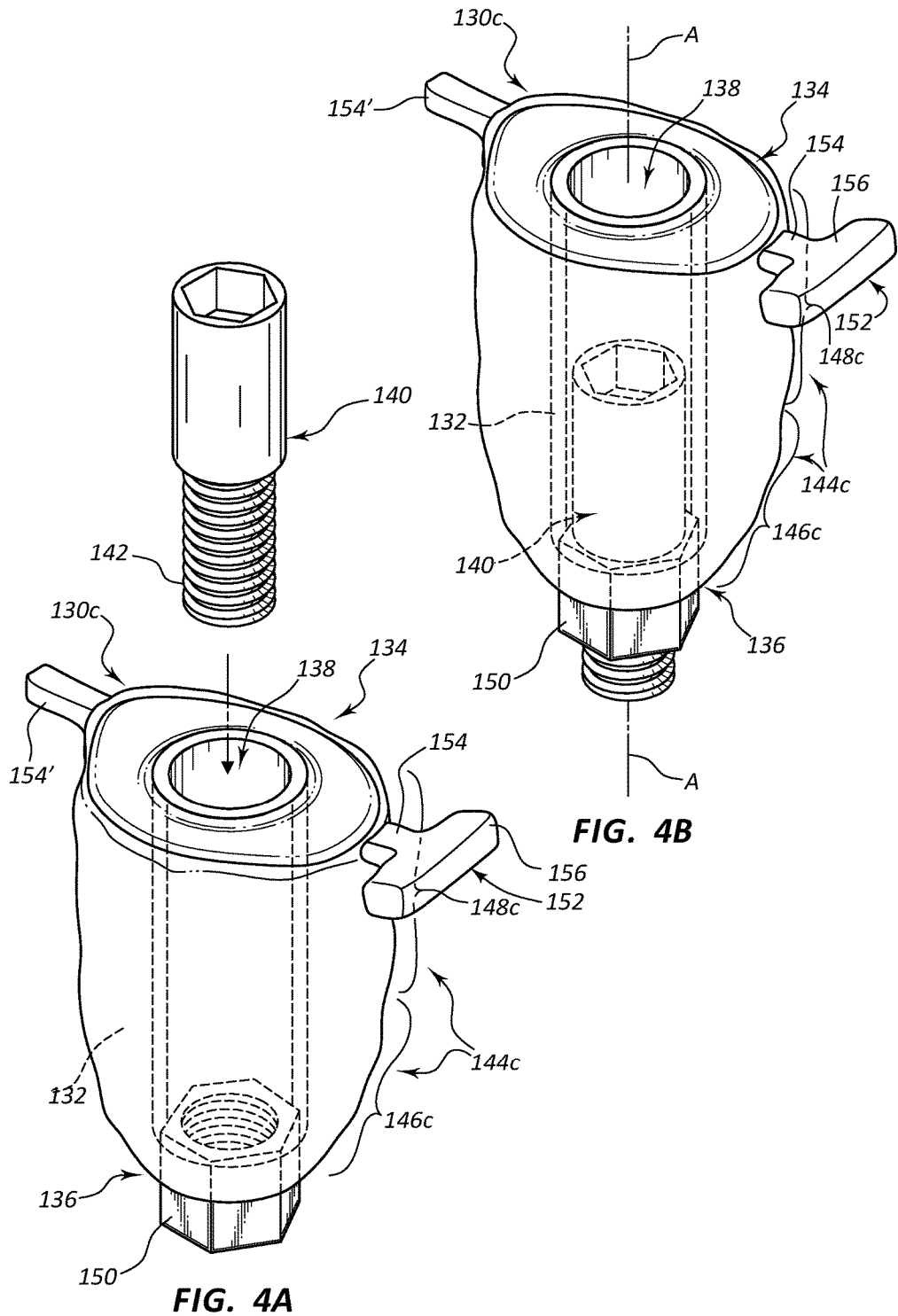
FIG. 4A is an exploded perspective view of a coupling screw and an anatomical healing abutment specifically configured for the upper cuspid tooth position.
FIG. 4B is an assembled perspective view of the anatomical healing abutment of FIG. 4A.
Figures 5A, 5B:
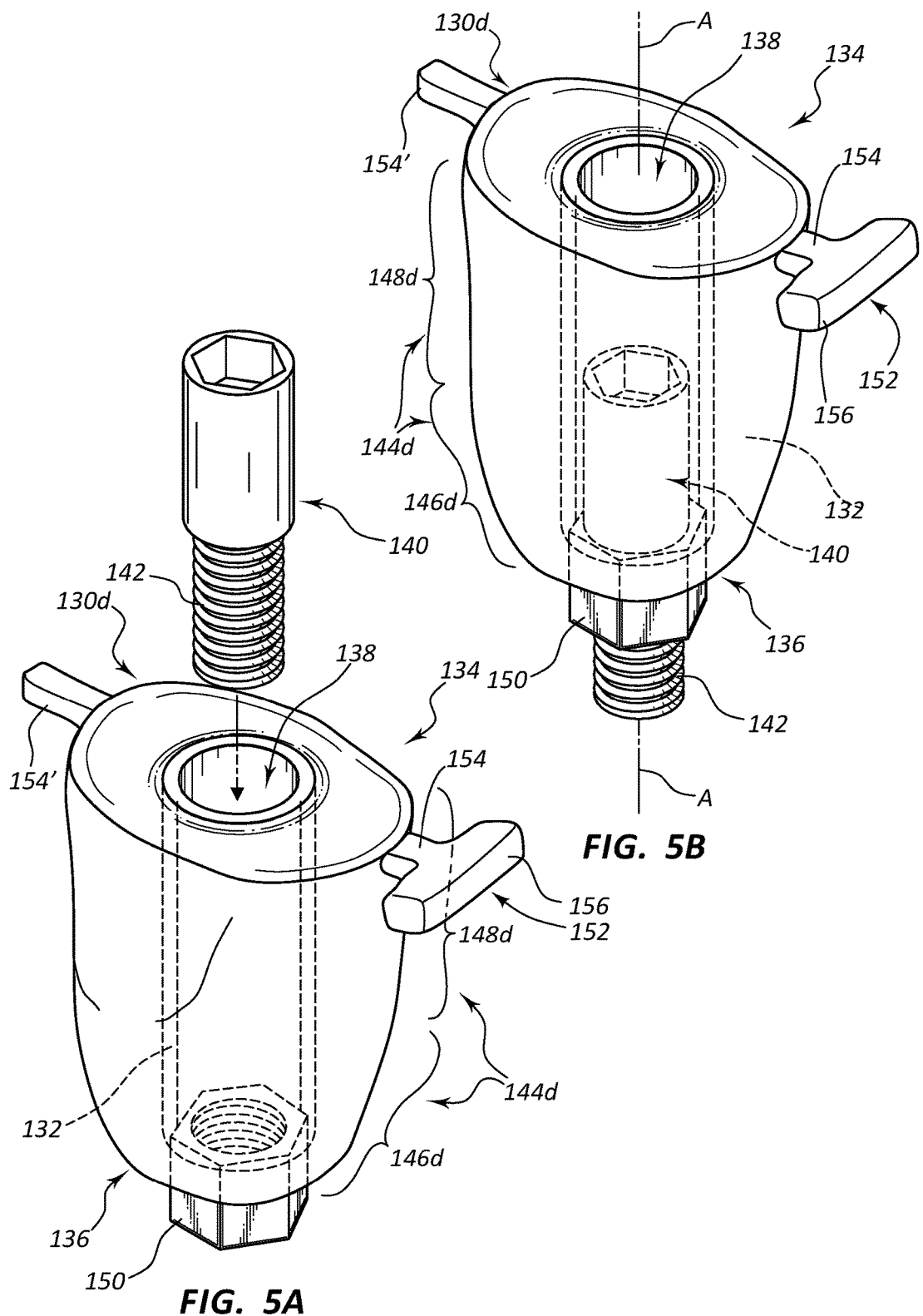
FIG. 5A is an exploded perspective view of a coupling screw and an anatomical healing abutment specifically configured for the upper bicuspid tooth position.
FIG. 5B is an assembled perspective view of the anatomical healing abutment of FIG. 5A.
Figures 6A, 6B:
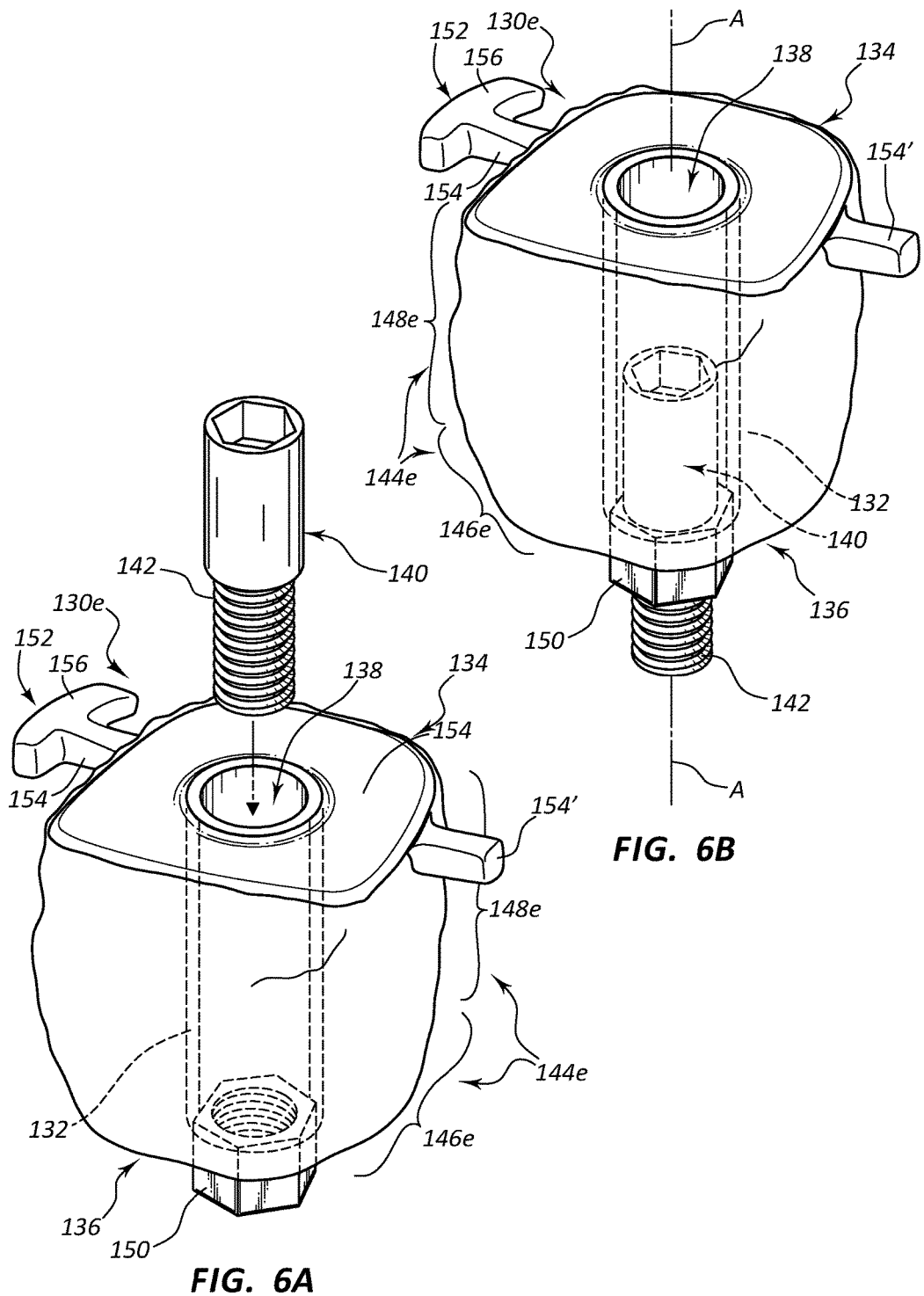
FIG. 6A is an exploded perspective view of a coupling screw and an anatomical healing abutment specifically configured for the upper molar tooth position.
FIG. 6B is an assembled perspective view of the anatomical healing abutment of FIG. 6A.

In another embodiment, the distal dental implant insertion end 136 may include a circular member 150' (see FIG. 2F). Of course, a circular member 150' does not lock against rotation. In another embodiment, no locking member at all is provided (see FIG. 2G). In the embodiment of FIG. 2G, external threads 142 are simply coupled into corresponding internal threads of dental implant 114, and the shape of subgingival portion 146*a* itself can serve to prevent rotation, as this portion is non-circular and engages against the gingival tissue bounding subgingival void 110. The presence of a directional alignment body as described herein may advantageously aid the practitioner in orienting healing abutment 130a in the proper rotational alignment with subgingival void 110 and implant 114. Other coupling mechanisms between the healing abutment and dental implant 114 are possible. For example, the location of internal and external threads may be switched (i.e., internal threads on healing abutment, and corresponding external threads on dental implant). Various other suitable coupling mechanisms will be apparent to one of skill in the art in light of the present disclosure.

A removable directional alignment body may be provided on cuff body 144a, as seen in the Figures (e.g., FIGS. 2A-2B). As shown, directional alignment body 152 may include a shaft 154 extending laterally (e.g., radially from axis A), beyond an outer perimeter of cuff body 144a. More specifically, when cuff body 144a is anatomically aligned relative to subgingival void 110 of the given tooth position of the patient, shaft 154 extends bucally beyond the outer perimeter of cuff body 144a. Buccal orientation of directional alignment body 152 (e.g., shaft 154) is beneficial, as it aids the practitioner in easily orienting the abutment 130a in the correct rotational orientation relative to void 110, which can be difficult without the reference provided by directional alignment body 152, particularly where the surgical site is bloody, and the structures of interest are relatively small, so that correct orientation can sometimes be difficult to ascertain.

As shown, directional alignment body 152 may be generally T-shaped, including a cross-bar 156 atop or near end of shaft 154. Cross-bar 156 advantageously may be disposed on the buccal side, beyond the outer perimeter of cuff body 144a, so as to easily allow the practitioner to pinch healing abutment 130a between a thumb and finger. Another alignment body (e.g., shaft 154') may be provided opposite shaft 154, providing two points disposed on opposite sides of cuff body for easy gripping between a thumb and finger of a single hand. Shafts 154 and 154' are substantially parallel to one another, extending from opposite sides of cuff body 144a. Such a thumb and finger arrangement allows the healing abutment to be easily rotated by rotating the thumb or finger relative to the other. Thus, the practitioner may easily orient the healing abutment with T-shaped directional alignment body 152 towards the buccal direction, and insert the subgingival portion 146a into the subgingival void, knowing that the abutment 130a is properly aligned. While manipulation may be achieved using a thumb and finger, it will be appreciated that shaft 154, shaft 154' cross-bar 156 and/or shaft 154' may alternatively be gripped by dental pliers or another suitable tool available to the practitioner during positioning and alignment of abutment 130a into subgingival void 110 and coupling into implant 114.

Once the anatomical healing abutment is correctly positioned and aligned within void 110 (e.g., and coupled into implant 114) directional alignment bodies 152 and/or 154' may be removed (e.g., cut away). T-shaped directional alignment body 152 may be removed first, after initial placement in the desired anatomically aligned orientation, while second directional alignment body 154' may be removed somewhat later, during final adjustments (e.g., as the crown portion 148a is being conformed and shaped to match the surrounding teeth, provide a desired floss width therebetween, etc.). Once the anatomical subgingival portion is anatomically aligned within the subgingival void, the healing abutment may be fixed to implant 114 in communication with void 110, e.g., with coupling screw 140. The directional alignment bodies are shown in) FIGS. 2A-2B, but omitted in FIGS. 2C-2G so as to better illustrate the other features of the healing abutment in those Figures. FIGS. 3A-6E follow the same pattern (showing the directional bodies in the "A" and "B" Figures, while omitting them in the others).

While the illustrated configuration is shown with cuff body 144a generally aligned with axis A of channel 138, in another embodiment, the axis A of channel 138 may be offset relative to an axis of cuff body 144a. Similarly, cuff body 144a may not be "on center" relative to axis A of threaded portion 142. This may be beneficial where the natural tooth (and thus void 110) is mis-aligned relative to what would be "normal". In another embodiment, in order to compensate for such mis-alignment of a tooth or implant, the cuff body may be intentionally mis-aligned relative to what would normally occur. For example, rather than aligning the directional alignment body so as to be perfectly buccally oriented upon insertion into void 110, it may be rotated slightly one direction or the other, to compensate for abnormalilty of placement in the implant. For example, where the locking structure 150 is hexagonal, the cuff body 144a may be rotated one face of hexagon 150 in a clock-wise or counter-clockwise direction to compensate. Where hexagon 150 has 6 equal faces, a rotation of one face equates to 60° off relative to a "true" buccal orientation. Similar adjustments may be possible for other locking structures (e.g., an octagon locking structure, etc.).

FIGS. 3A-3E illustrate various views of an exemplary anatomical healing abutment 130b configured for use at the upper lateral incisor tooth position. Anatomical healing abutment 130b is similar to healing abutment 130a, but includes a differently shaped cuff body 144b, subgingival portion 146b, and emergent crown portion 148b. In particular, subgingival portion 146b is particularly shaped to anatomically fill and shape the subgingival void associated with an upper lateral incisor. Although the particular size and shape of subgingival portion 146b is different from that of subgingival portion 146a, both include an asymmetric cross-section occlusally flared profile, each being particularly configured to mimic the subgingival portion of the particular tooth position they are associated with.

FIGS. 4A-4E illustrate various views of an exemplary anatomical healing abutment 130c configured for use at the upper cuspid tooth position. Anatomical healing abutment 130c is similar to healing abutment 130a, but includes a differently shaped cuff body 144c, subgingival portion 146c, and emergent crown portion 148c. In particular, subgingival portion 146c is particularly shaped to anatomically fill and shape the subgingival void associated with an upper cuspid. Although the particular size and shape of subgingival portion 146c is different from that of subgingival portion 146a, both include an asymmetric cross-section and an occlusally flared profile, each being particularly configured to mimic the subgingival portion of the particular tooth position they are associated with.

FIGS. 5A-5E illustrate various views of an exemplary anatomical healing abutment 130d configured for use at the upper bicuspid tooth position. Anatomical healing abutment 130d is similar to healing abutment 130a, but includes a differently shaped cuff body 144d, subgingival portion 146d, and emergent crown portion 148d. In particular, subgingival portion 146d is particularly shaped to anatomically fill and shape the subgingival void associated with an upper bicuspid. Although the particular size and shape of subgingival portion 146d is different from that of subgingival portion 146a, both include an asymmetric cross-section and occlusally flared profile, each being particularly configured to mimic the subgingival portion of the particular tooth position they are associated with.

FIGS. 6A-6E illustrate various views of an exemplary anatomical healing abutment 130e configured for use at the upper molar tooth position. Anatomical healing abutment 130e is similar to healing abutment 130a, but includes a differently shaped cuff body 144e, subgingival portion 146e, and emergent crown portion 148e. In particular, subgingival portion 146e is particularly shaped to anatomically fill and shape a subgingival void associated with an upper molar. Although the particular size and shape of subgingival portion 146e is different from that of subgingival portion 146a, both include an asymmetric cross-section and occlusally flared profile, each being particularly configured to mimic the subgingival portion of the particular tooth position they are associated with.

The illustrated shapes for various cuff bodies, and particularly subgingival portions 146 are exemplary. To those of skill in the art, and in light of the present disclose, it will be apparent that a single configuration may be suitable for two or more different tooth positions. For example, the illustrated bicuspid configuration of FIGS. 5A-5E may be suitable for use with both the first and second bicuspids. Similarly, the illustrated molar configuration of FIGS. 6A-6E may be suitable for use with both first and second molars. A single lower incisor configuration may be used for all four lower incisors. A similar set of healing abutments, with appropriately sized and shaped cuff bodies (including subgingival portions) may similarly be provided for each of the unique shaped subgingival portions associated with the lower dental arch. In addition, in some instances, there may be some difference between the healing cuff configuration of a particular tooth position of the right side of a given dental arch versus the left side of the same dental arch.

A kit of anatomical healing abutments may be provided, which may include a plurality of differently sized and shaped healing abutments corresponding to subgingival voids of different tooth positions. For example, the provided abutments may include a healing abutment 130a, 130b configured for treating a subgingival void of an incisor position (FIGS. 2-3), a healing abutment 130c, 130d configured for treating a subgingival void of an cuspid or bicuspid position (FIGS. 4-5), and a healing abutment 130e for treating a subgingival void of a molar position (FIG. 6). The subgingival portions of each of the healing abutments may be configured to anatomically fill and shape the subgingival void of the corresponding tooth position, and support the gingival tissue around the subgingival void to prevent or minimize slump of gingival tissue into the void, as described. Each of the emergent crown portions of the abutments may have a mesial-distal width so as to span a width of the gingival margin, and an occlusal height so as to extend occlusally beyond the gingival margin of the corresponding tooth position, as described, preventing unwanted migration of adjacent teeth towards the surgical site.

Figure 7A:
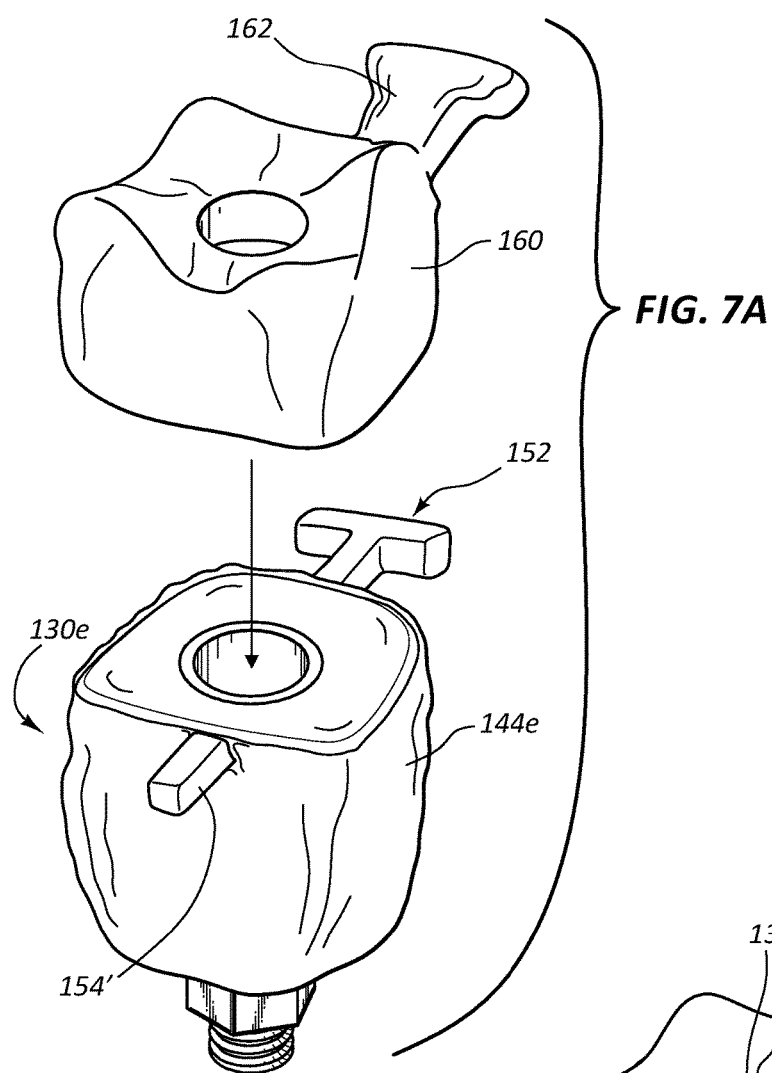
FIG. 7A is an exploded perspective view showing a related system including an anatomical healing abutment and an associated temporary crown.
Figure 7B:
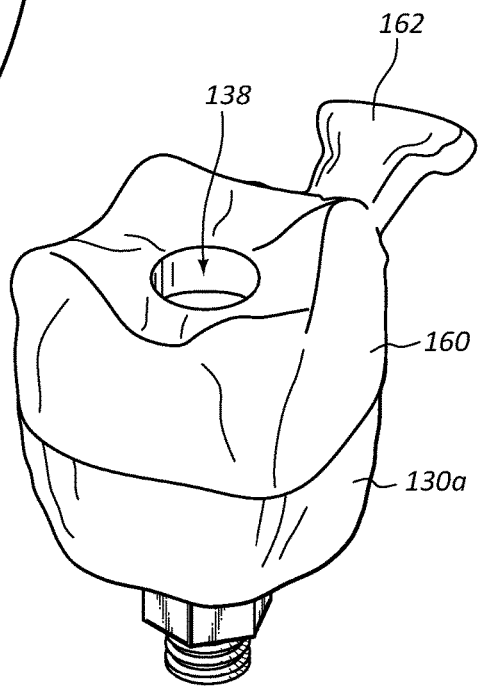
FIG. 7B is a perspective view showing the system of FIG. 7A with the temporary crown attached over the anatomical healing abutment.

FIGS. 7A-7B illustrate bonding of a temporary crown over the healing abutment. While illustrated with respect to a molar position, it will be appreciated that any tooth position may be provided with a crown. Many practitioners will not place a temporary provisional crown when the healing abutment is placed or even after the healing abutment has been in place for an extended period of time because it can be time consuming and troublesome. A temporary crown may be formed or provided. In an embodiment, the temporary crown may be formed as described in the inventors' own earlier U.S. application Ser. No. 14/327, 869, already incorporated by reference. For example, a temporary crown 160 may be luted or otherwise bonded to an appropriate anatomical healing abutment (e.g., 130e). Before bonding, a portion or even all of the emergent crown portion of the anatomical healing abutment may be removed, if desired, so that the resulting combination structure has the proper occlusal height. For example, it may be reduced in height just prior to installation, or even after installation, while in place. The anatomical healing abutment positioned within the subgingival void and anchored to the dental implant may have the crown 160 placed thereover, a luting cement or other suitable bonding material may be disposed therebetween, the patient may be instructed to gently bite down on the crown seated on the anatomical healing abutment, and the bonding material (e.g., a light curable adhesive) may be cured (e.g., exposed to a dental curing light), securing the temporary crown in place. The practitioner may cut off any burrs, flashing, a directional alignment body 162 of crown 160, or perform any other quick preparation or shaping of the crown after bonding with a dental burr or other tool, before or after placement over the anatomical healing abutment. As shown, in an embodiment, directional alignment body 162 may be provided on just the buccal side of crown 160. Alternatively, two oppositely disposed directional alignment bodies could be provided, as illustrated relative to the healing abutments. Body 162 may be removed from crown 160, e.g., once crown 160 is bonded to healing abutment 130e.

Other kits, systems, and methods for placement of a temporary crown may be used. For example, in another embodiment, a hollow temporary crown form may be employed, as described in International Application No. PCT/US2013/020992, already incorporated by reference.

In any case, in some circumstances, it may be possible to place a temporary crown or similar prosthesis during first stage treatment, at the time of initial placement of the healing cap, immediately after pulling the tooth. In other embodiments, it may be desirable to allow the site to heal somewhat, after which the patient may return and the temporary crown installed.

FIGS. 1A-1E discussed above show the same steps to be taken when installing the anatomical healing abutments of the present invention. As shown in FIGS. 1A-1E, the tooth is removed, the void 108 including an implant void portion and subgingival void 110 is prepared to receive dental implant 114, and dental implant 114 is anchored into the underlying bony tissue of the jaw bone. Rather than installing the cylindrical state of the art commercially available healing abutment shown in FIG. 1F, the appropriate anatomical healing abutment is selected (e.g., healing abutment 130a configured for anatomically filling and shaping the subgingival void 110 of an upper central incisor).

Figure 8A:
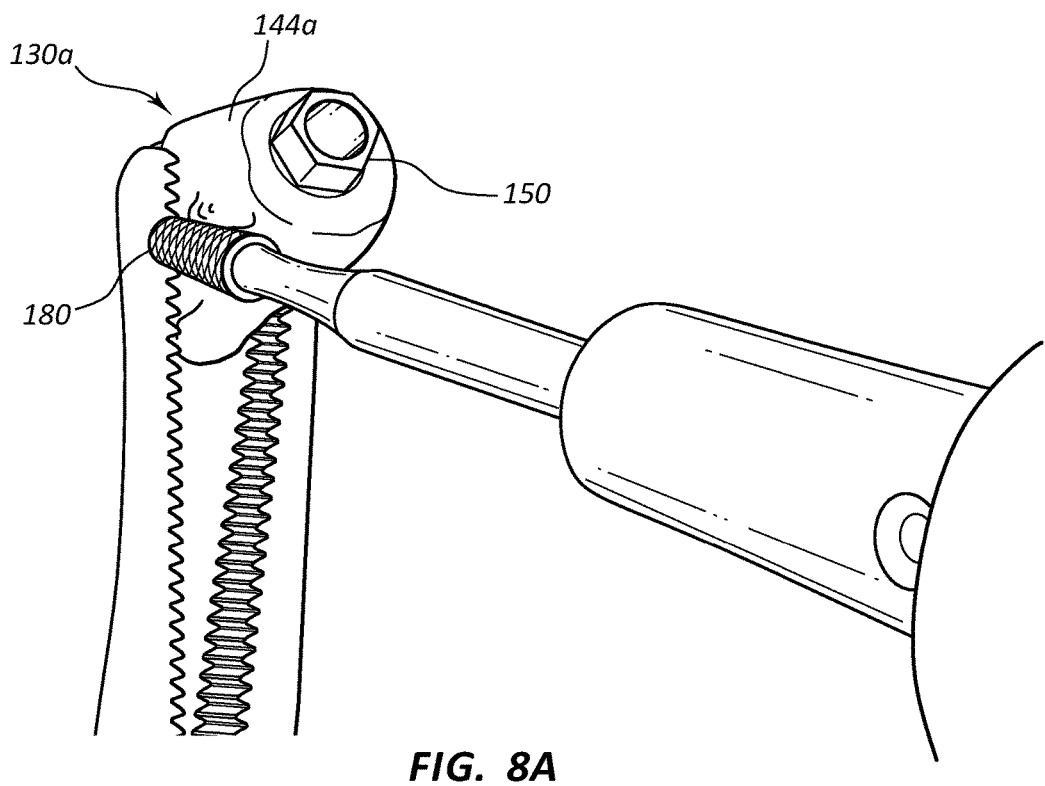
FIG. 8A is a perspective view showing a portion of the cuff body of a healing abutment being customized by removal with a dental burr.
Figure 8B:
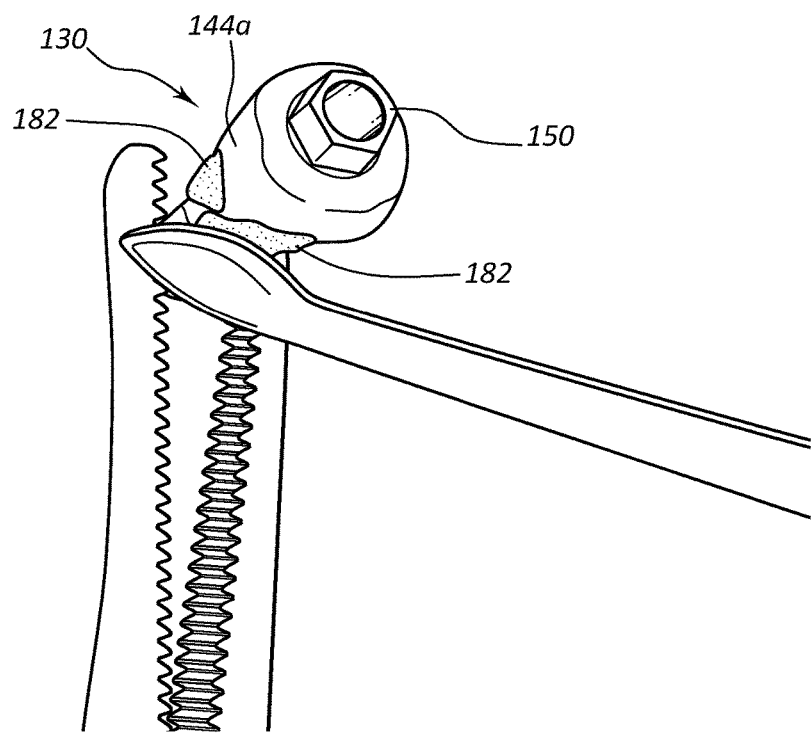
FIG. 8B is a perspective view showing the cuff body being customized by building up with application of a dental material (e.g., a curable dental material)
Figure 8C:
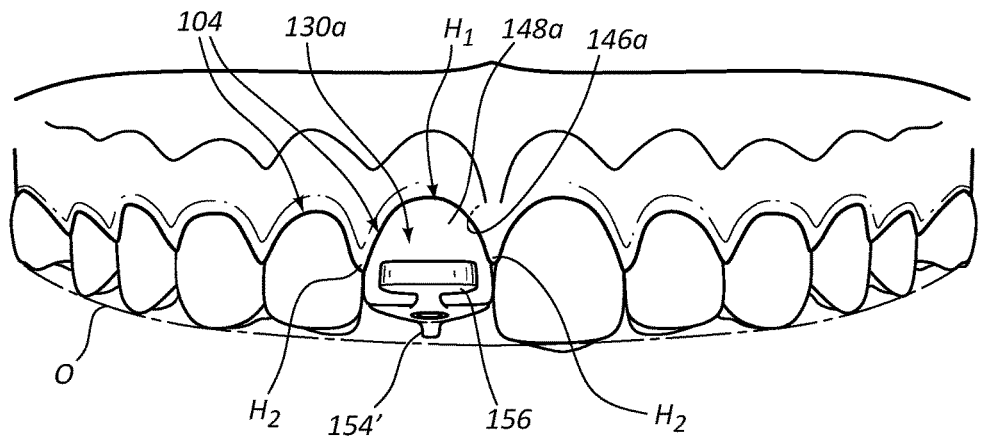
FIG. 8C is a perspective view of an upper dental arch in which an anatomical healing abutment according to the present invention has been coupled into a corresponding implant of the central incisor tooth position, illustrating the mesial-distal) width and occlusal height of the emergent crown portion of the abutment after installation.
Figure 8D:
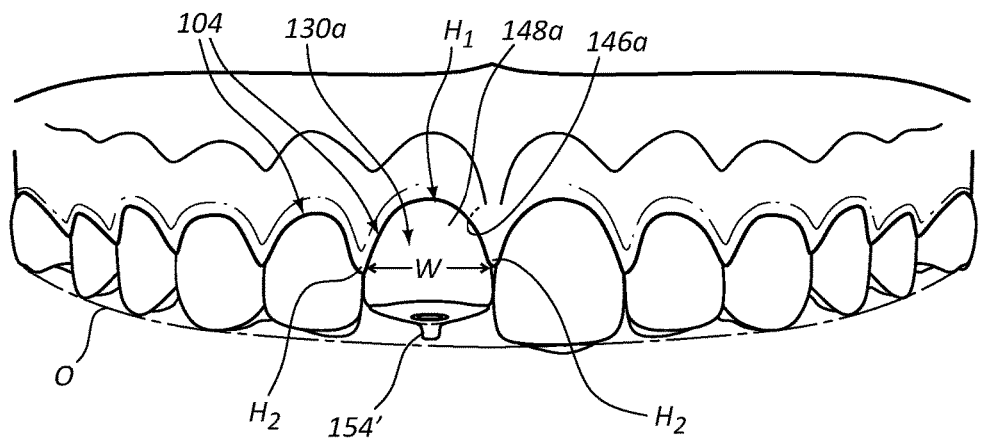
FIG. 8D is a perspective view similar to that of FIG. 8C, once the T-shaped buccal alignment body has been removed, allowing the inside of the lip or cheek to comfortably contact the cuff body of the abutment, while the lingual alignment body remains to still provide an alignment function.
Figure 8E:
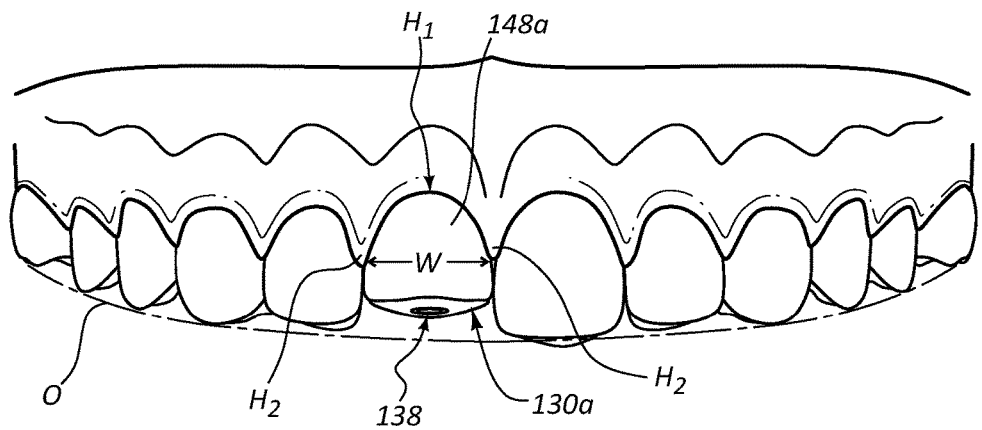
FIG. 8E is another perspective view of the arch of FIG. 8D showing the visible emergent crown portion extending above the gingival margin along the entire gingival perimeter, once both directional alignment bodies have been removed.

The as mass-manufactured shape and contours, which are a very close fit to the actual subgingival void 110, may be custom modified as shown in FIG. 8A by removing select portions of cuff body 144a (particularly subgingival portion 146a) with a dental burr 180 or other suitable tool. As shown in FIG. 8B, if necessary, the practitioner may build up portions of cuff body 144a (particularly subgingival portion 146a) by applying and curing a dental material (e.g., light-curable, chemically-curable, heat curable, or other adhering dental material) 182. This is possible because at least the subgingival portion 146a of cuff body 144a is formed of plastic or another easily removable material, which also strongly bonds to a dental material used for build-up, so that shaving down and/or building up is easily achieved. By removing material, adding material, or both, the practitioner is advantageously able to relatively quickly customize at least the subgingival portion 146a of the cuff body 144a so that it provides a perfect or near perfect fit, anatomically filling the subgingival void 110, with substantially no gaps.

Examples of materials that may be employed as a "build-up" material include, but are not limited to glass ionomer cements, zinc polycarboxylate cements, and acrylic based curable compositions, for example, ACCESS CROWN, available from Centrix, located in Shelton, Conn. In one embodiment, the curable or otherwise settable dental material may comprise a radiopaque filler in order to provide radiopacity.

As shown in FIG. 8C, the subgingival portion 146a of healing abutment 130a is placed within subgingival void 110 so that subgingival portion 146a fills the void 110 with substantially no gaps shaping and providing a support surface against which the gingival tissue bounding void 110 is supported, preventing such tissue from slumping into void 110. Furthermore, emergent crown portion 148a has a mesial-distal width so as to span the width of the gingival margin 104, and an occlusal height so as to extend occlusally beyond the gingival margin 104. As a result of such full and complete support, the gingival margin features, such as the dynamic range of the height of contour, the interdental papilla, and other aesthetic features are preserved, e.g., substantially identical to that provided by the natural tooth prior to its removal. In an embodiment, 70% or more, 75% or more, 80% or more, 85% or more, 90% or more, 95% or more (e.g., 100%) of the original natural or desired height of contour is preserved. The emergent crown portion 148a extends from the gingival margin occlusally upward, which is helpful in ensuring that all gingival tissue is fully supported, particularly where there may be some small degree of variability in the contours of this gingival tissue between one patient and another for a given tooth position.

As seen in FIG. 8C, both directional alignment bodies 152 and 154' may still be present, having been employed to position, align, and orient abutment 130a so that subgingival portion 146a is anatomically aligned within subgingival void 110. The presence of the directional alignment bodies makes it easy for the practitioner to ensure that proper rotation is achieved before advancing the coupling screw of each abutment into its corresponding implant 114.

FIG. 8D shows only T-shaped alignment body 152 removed, while lingual alignment body 154' remains. In FIG. 8E, both alignment bodies 152 and 154' have been removed. For example, removal of body 152 once abutment 130a has been anatomically oriented within subgingival void may provide greater comfort, allowing the patient's lip or cheek to contact the crown portion 148a of cuff body 144a. Lingual alignment body 154' may remain, e.g., until final adjustments are made, and it is removed. While it remains, it continues to provide an alignment function and reference.

FIG. 8E perhaps best shows how the width and height of emergent crown portion 148a of the abutment is sufficient so that the width of the crown portion 148a spans the corresponding width of the gingival margin, around the perimeter of margin gingival 104. In addition to providing such "full" width, crown portion 148a has an occlusal height that extends occlusally beyond the gingival margin 104 at all locations across the width (e.g., not a configuration such as in US2002/0064758 to Lee where only a central post extending occlusally is provided, which post provides no gingival support). Because the full width includes such an occlusal height, the crown portion 148a serves as a spacer relative to adjacent teeth, preventing them from migrating inwardly towards healing abutment 130a. For example, the width may be similar to that provided by the natural, anatomically correct tooth, with a 0.5 to 1 mm space on either side between the crown portion 148a and any adjacent tooth, so as to provide just sufficient space for flossing. For example, the mesial-distal width of the emergent crown portion may span the outer perimeter of the void within the gingival margin. The mesial-distal width of the emergent crown portion may be 5 mm to about 10.5 mm (e.g., at the height of contour).

In an embodiment, the crown portion 148a may extend occlusally at least 2 mm, at least 3 mm, or at least 5 mm beyond mesial trough (H1) of gingival margin 104. Similarly, the crown portion 148a may extend occlusally at least 1 mm, at least 2 mm, at least 3 mm, at least 4 mm, or at least 5 mm beyond the height of contour ($H_2$), ensuring that all gingival tissue is fully supported, and that any adjacent teeth are prevented from migrating towards the surgical site. The crown portion 148a may have an occlusal height that extends within at least 5 mm, within at least 3 mm, or within at least 2 mm of the occlusal bite plane "O". Where a temporary crown is bonded over cuff body 144a, the occlusal top of the crown may of course reach the occlusal plane.

FIG. 8E shows the directional alignment bodies 152 and 154' having been removed (e.g., they may be easily cut away with a burr or other convenient dental tools once anatomical alignment has been achieved).

Figure 8F:
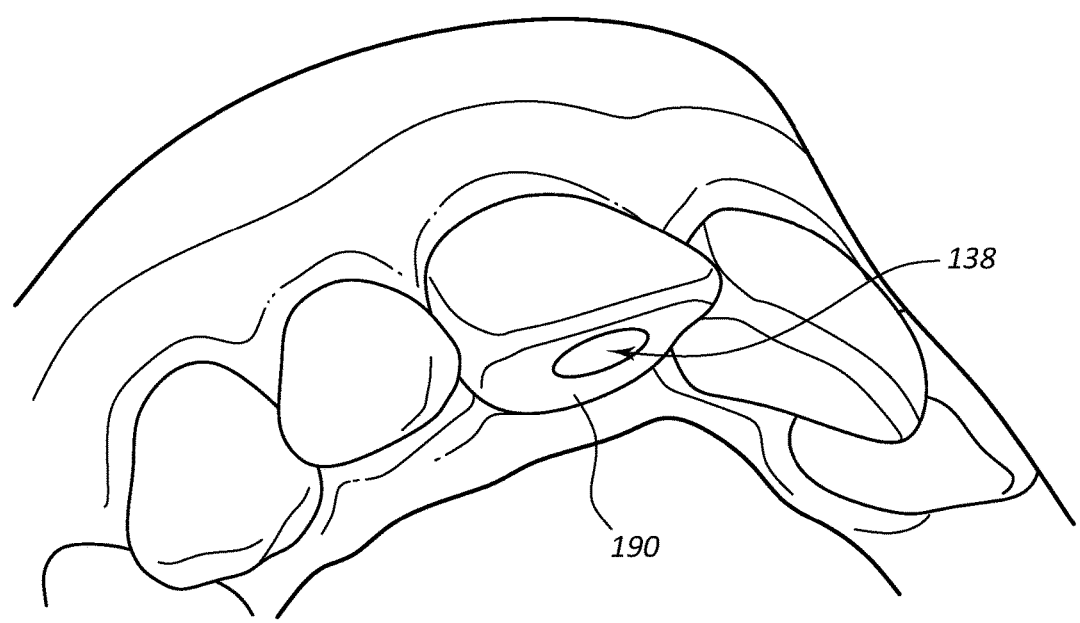
FIG. 8F is another perspective view of the arch of FIG. 8C-8E in which a temporary crown has been attached over the healing abutment while preserving access to the hollow channel of the healing abutment.

As shown in FIG. 8F, a temporary crown 190 may be attached over the anatomical healing abutment 130a, while preserving access to underlying hollow channel 138 of healing abutment 130a (e.g., a hole may be drilled or otherwise provided within temporary crown 190).

It may be desired to remove the cuff body 144a from the subgingival void 110 some time after initial installation, e.g., after at least some degree of healing has occurred, in order to take an impression in preparation for placement of a permanent crown or other prosthesis. For example, the cuff body 144a may be removed from void 110, a dental post may be installed within void 110, and an impression of the post and surrounding gingival and dental tissue may be taken (e.g., 2-3 weeks after placement of the abutment). The post may be removed, and the cuff body reinstalled into the void so that healing may continue (e.g., until 2-4 months after initial abutment placement), when the permanent crown or other prosthesis may be installed. In some embodiments, the impression may be taken digitally, e.g., by digital scanning or appropriate imaging process (e.g., CT scan, ultrasound, etc.) of the patient. For such scans, it may not be necessary to actually remove the cuff body from the subgingival void, as the scan may be taken while the cuff body is in place. Radiopaque markers or materials as described herein may be provided to aid in such scanning. Thus, as used herein, the phrase "taking an impression" or similar may refer to a physical impression taken using an impression material or to digital scanning. In either case, a model (e.g., physical or digital) may be created for use in forming a permanent crown or other prosthesis. At an appropriate time, a portion of the emergent crown portion may be removed in order to contour the crown portion, and approximate a size or shape of a tooth (e.g., in place of, or while installing a provisional crown as in FIGS. 7A-7B).

When a permanent crown (typically custom prepared in an off-site dental lab) is ready for installation, the coupling screw may simply be backed out from implant 114 through channel 138, allowing removal of the abutment and temporary crown. A permanent crown post or the distal end of the permanent crown may then be coupled into implant 114, and the distal end of the permanent crown may include a shape that takes the place of subgingival portion 146a of healing abutment 130a. This may continue to ensure that the gingival tissue surrounding void 110 which has been preserved through the use of anatomical healing abutment 130a can continue to be preserved.

The use of the anatomical healing abutment provides for the preservation of various gingival features that are characteristic of natural teeth, including the gingival margin, including its height of contour, the dynamic range of the height of contour, the interdental papilla, the buccal prominence, and other desired, "normal", natural, aesthetic features. These features are typically progressively lost over the weeks and/or months following first stage treatment where insufficient structure is provided for supporting the gingival tissue at the surgical site where the tooth once was. Use of the present inventive healing abutments, kits, and methods allow these features to be maintained, rather than progressively lost following first stage treatment and before placement of a custom permanent crown.

It will be appreciated that some embodiments may not necessarily employ a socket at a distal end of the well configured to releasably receive therein a dental implant. For example, a so-called pontic may require no coupling to a dental implant, as the pontic may be positioned into the prepared void in the patient's jaw bone (without the need for any anchoring implant). The pontic may rather be anchored to adjoining teeth on one or both sides of the pontic. Such pontics would be similar to healing abutments such as those described herein, but would not require any mechanism for coupling to a dental implant. Because no coupling to an implant is required, no central access channel 138 may be needed. Thus, the pontic may be solid, without any hollow access channel. Such pontics are within the scope of the presently described healing abutments.

As used in this specification and the appended claims, the singular forms "a," "an" and "the" include plural referents unless the context clearly dictates otherwise.

The present invention can be embodied in other specific forms without departing from its spirit or essential characteristics. Thus, the described implementations are to be considered in all respects only as illustrative and not restrictive. The scope of the invention is, therefore, indicated by the appended claims rather than by the foregoing description. All changes that come within the meaning and range of equivalency of the claims are to be embraced within their scope.

The invention claimed is:

1. An anatomical healing abutment configured for promoting healing of gingival tissue around a subgingival void of a given tooth position and shaping of a gingival margin of a patient at the given tooth position, comprising:
   a cuff body having an anatomical subgingival portion extending from an implant end to the gingival margin of the patient, and an emergent crown portion extending from the subgingival portion and occlusally beyond the gingival margin of the patient; and
   a directional alignment body extending from an outer perimeter of the cuff body, on a buccal side of the cuff body, the directional alignment body being disposed on the buccal side of the cuff body so as to confirm to a practitioner that the anatomical healing abutment is properly rotationally aligned relative to an implant during installation of the anatomical healing abutment in the implant, wherein the directional alignment body comprises a T-shaped directional alignment body, the anatomical healing abutment further comprising a second alignment body also extending from the cuff body, but oriented about 180° away from the directional alignment body, so as to be on the lingual side of the cuff body, the second alignment body being a single shaft rather than being T-shaped,
   wherein the anatomical subgingival portion has an asymmetric cross section and an outer surface that is shaped to provide substantially custom filling of at least an emergence portion of the subgingival void where a natural tooth once emerged from the void, or where a tooth would have emerged from the void, the subgingival portion thus being shaped to anatomically fill and fully support gingival tissue around the subgingival void to prevent or minimize slump of gingival tissue into the subgingival void,
   wherein the emergent crown portion has a mesial-distal width so as to span a width of the gingival margin, a maximum of the mesial-distal width being greater than a maximum mesial-distal width of the subgingival portion, the emergent crown portion having an occlusal height so as to extend occlusally beyond the gingival margin.

2. An anatomical healing abutment configured for promoting healing of gingival tissue around a subgingival void of a given tooth position and shaping of a gingival margin of a patient at the given tooth position, comprising:
   a cuff body having an anatomical subgingival portion extending from an implant end to the gingival margin of the patient, and an emergent crown portion integrally formed with the subgingival portion and extending beyond the gingival margin of the patient;
   a directional alignment body extending from an outer perimeter of the cuff body, on a buccal side of the cuff body, the directional alignment body being disposed on the buccal side of the cuff body so as to confirm to a practitioner that the anatomical healing abutment is properly rotationally aligned relative to an implant during installation of the anatomical healing abutment in the implant, wherein the directional alignment body comprises a T-shaped directional alignment body, the anatomical healing abutment further comprising a second alignment body also extending from the cuff body, but oriented about 180° away from the directional alignment body, so as to be on the lingual side of the cuff body, the second alignment body being a single shaft rather than being T-shaped,
   wherein the anatomical subgingival portion has an asymmetric cross section and an outer surface that is shaped to provide substantially custom filling of at least an emergence portion of the subgingival void where a natural tooth once emerged from the void, or where a tooth would have emerged from the void, the subgingival portion thus being shaped to anatomically fill and fully support gingival tissue around the subgingival void to prevent slump of gingival tissue into the subgingival void during healing so as to substantially maintain or increase a height of contour of the gingival margin,
   wherein the emergent crown portion has an occlusal height so as to extend to at least the height of contour of the gingival margin and a mesial-distal width so as to span a width of the gingival margin at the height of contour, a maximum of the mesial-distal width of the emergent crown portion being greater than a maximum mesial-distal width of the subgingival portion.

3. An anatomical healing abutment as in claim 2, wherein the emergent crown portion has an occlusal height so as to extend beyond the height of contour.

4. An anatomical healing abutment as in claim 2, wherein the emergent crown portion has an occlusal height so as to extend occlusally at least 2 mm beyond a mesial trough of the gingival margin.

5. An anatomical healing abutment as in claim 2, wherein the emergent crown portion has an occlusal height so as to extend occlusally at least 3 mm beyond a mesial trough of the gingival margin.

6. An anatomical healing abutment as in claim 2 wherein the emergent crown portion has an occlusal height so as to extend within at least 5 mm of the occlusal plane.

7. An anatomical healing abutment as in claim 2, wherein the emergent crown portion has an occlusal height so as to extend within at least 3 mm of the occlusal plane.

8. A kit including an anatomical healing abutment as in claim 2 and a temporary crown that is selectively attachable to the cuff body.

9. A kit of anatomical healing abutments configured for promoting healing of gingival tissue around a subgingival void of a given tooth position and shaping of a gingival margin of a patient at the given tooth position, comprising:
   a plurality of differently sized and shaped healing abutments corresponding to subgingival voids of different tooth positions,
      a first healing abutment configured for treating a subgingival void of an incisor position,
      a second healing abutment configured for treating a subgingival void of a cuspid or bicuspid position, and
      a third healing abutment configured for treating a subgingival void of a molar position,
   each healing abutment comprising:
      a cuff body having an anatomical subgingival portion extending from an implant end to a gingival margin of the corresponding tooth position and an emergent crown portion extending from the subgingival portion and occlusally beyond the gingival margin,
   directional alignment body extending from an outer perimeter of the cuff body, on a buccal side of the cuff body, the directional alignment body being disposed on the buccal side of the cuff body so as to confirm to a practitioner that the anatomical healing abutment is properly rotationally aligned relative to an implant during installation of the anatomical healing abutment in the implant, wherein the directional alignment body comprises a T-shaped directional alignment body, the anatomical healing abutment further comprising a second alignment body also extending from the cuff body, but oriented about 180° away from the directional alignment body, so as to be on the lingual side of the cuff body, the second alignment body being a single shaft rather than being T-shaped,
   wherein the anatomical subgingival portion of the cuff body has an asymmetric cross section and an outer surface that is shaped to provide substantially custom filling of at least an emergence portion of the subgingival void where a natural tooth once emerged from the void, or where a tooth would have emerged from the void, the subgingival portion thus being shaped to anatomically fill and shape the subgingival void of the corresponding tooth position and fully support gingival tissue around the subgingival void to prevent or minimize slump of gingival tissue into the subgingival void, and
   wherein the emergent crown portion has a mesial-distal width so as to span a width of the gingival margin, a maximum of the mesial-distal width being greater than a maximum mesial-distal width of the subgingival portion, the emergent crown portion having an occlusal height so as to extend occlusally beyond the gingival margin of the corresponding tooth position.

* * * * *